US010575526B2

(12) United States Patent
Clinton et al.

(10) Patent No.: US 10,575,526 B2
(45) Date of Patent: Mar. 3, 2020

(54) METHODS FOR CONTROLLING PLANT PATHOGENS USING N-PHOSPHONOMETHYLGLYCINE

(71) Applicant: Monsanto Technology LLC, St. Louis, MO (US)

(72) Inventors: William P. Clinton, University City, MO (US); Paul C. C. Feng, Creve Coeur, MO (US); James F. Mitchell, Cleveland, MS (US); David V. Uhr, Henderson, KY (US)

(73) Assignee: Monsanto Technology LLC, St. Louis, MO (US)

( * ) Notice: Subject to any disclaimer, the term of this patent is extended or adjusted under 35 U.S.C. 154(b) by 169 days.

(21) Appl. No.: 14/835,612

(22) Filed: Aug. 25, 2015

(65) Prior Publication Data

US 2016/0081345 A1 Mar. 24, 2016

Related U.S. Application Data

(62) Division of application No. 11/061,681, filed on Feb. 22, 2005, now abandoned.

(60) Provisional application No. 60/557,403, filed on Mar. 30, 2004, provisional application No. 60/622,134, filed on Oct. 26, 2004, provisional application No. 60/654,442, filed on Feb. 18, 2005.

(51) Int. Cl.
*A01N 57/20* (2006.01)
*A01N 25/00* (2006.01)
*C12N 15/82* (2006.01)

(52) U.S. Cl.
CPC ......... *A01N 57/20* (2013.01); *C12N 15/8275* (2013.01); *C12N 15/8281* (2013.01); *C12N 15/8282* (2013.01)

(58) Field of Classification Search
None
See application file for complete search history.

(56) References Cited

U.S. PATENT DOCUMENTS

| | | | | |
|---|---|---|---|---|
| 3,799,758 | A | 3/1974 | Franz | |
| 3,853,530 | A | 12/1974 | Franz | |
| 3,977,860 | A | 8/1976 | Franz | |
| 4,405,531 | A | 9/1983 | Franz | |
| 4,808,628 | A | 2/1989 | Shepard et al. | |
| 4,840,659 | A | 6/1989 | Franz | |
| 5,110,805 | A | 5/1992 | Berner et al. | |
| 5,558,071 | A | 9/1996 | Ward et al. | |
| 6,083,878 | A | 7/2000 | Brants et al. | |
| 6,468,944 | B1 | 10/2002 | Bugg et al. | |
| 6,579,851 | B2 | 6/2003 | Goeke et al. | |
| 6,753,339 | B1 | 6/2004 | Chazalet et al. | |
| 7,098,170 | B2 | 8/2006 | Asrar et al. | |
| 7,250,561 | B1 | 7/2007 | Pallett et al. | |
| 7,572,950 | B2 | 8/2009 | Herbers et al. | |
| 7,608,761 | B2 | 10/2009 | Baley et al. | |
| 7,622,641 | B2 | 11/2009 | McCutchen et al. | |
| 7,838,464 | B2 * | 11/2010 | Oakley | A01N 57/20 504/118 |
| 8,361,928 | B2 | 1/2013 | Baley et al. | |
| 8,461,129 | B2 | 6/2013 | Bolduc et al. | |
| 8,735,348 | B2 | 5/2014 | Sidelman | |
| 2003/0049814 | A1 | 3/2003 | Andrews et al. | |
| 2007/0010401 | A1 | 1/2007 | Noon et al. | |
| 2007/0197474 | A1 | 8/2007 | Clinton et al. | |
| 2009/0023687 | A1 | 1/2009 | Haas | |
| 2011/0028412 | A1 | 2/2011 | Cappello et al. | |
| 2012/0135966 | A1 | 5/2012 | Kohn et al. | |
| 2013/0031004 | A1 | 1/2013 | Dorsey et al. | |
| 2013/0084243 | A1 | 4/2013 | Goetsch et al. | |

FOREIGN PATENT DOCUMENTS

| | | | | |
|---|---|---|---|---|
| BR | 0415808-3 A | 10/2004 | | |
| CA | 2611178 | 12/2006 | | |
| DE | 100 59 609 | 6/2002 | | |
| ES | 396223 | 3/1975 | | |
| WO | WO 1997/36488 | 10/1997 | | |
| WO | WO-2004043150 A1 | * | 5/2004 | A01N 57/20 |
| WO | WO 2004/043150 | 6/2005 | | |
| WO | WO 2005/041669 | 9/2005 | | |
| WO | WO 2006/131230 | 5/2006 | | |
| WO | WO 2007/017256 | 11/2007 | | |
| WO | WO 2008/116730 | 10/2008 | | |
| WO | WO 2008/129060 | 10/2008 | | |
| WO | WO 2008/049575 | 5/2009 | | |
| WO | WO 2010/135324 A1 | 11/2010 | | |

OTHER PUBLICATIONS

Njiti et al. (Roundup Ready soybean: glyphosate effects on Fusarium solani root colonization and sudden death syndrome, Agronomy journal (2003), vol. 95, No. 5, pp. 1140-1145) (Year: 2003).*
Grossbardet al.( The action of Gramoxone W and Roundupon cereal pathogens, Mededelingen Fakulteit Landbouwwetenschappen, Gent(1976),vol. 41, No. 2, I, pp. 693-702, 12 refs. (Year: 1976).*
El-Sayed(Efficiency of biocontrol agents tocontrol fusarial diseases of watermelon as influenced by herbicide Roundup( AssiutJournal of Agricultural Sciences (2003), vol. 34, No. 2, pp. 225-239, 41 refs.) (Year: 2003).*
Morjan et al.( Fungicidal effects of glyphosate and glyphosate formulations on four species of entomopathogenic fungi., Environmental Entomology, (Dec. 2002) vol. 31, No. 6, pp. 1206-1212. Print) (Year: 2002).*

(Continued)

*Primary Examiner* — Alton N Pryor
(74) *Attorney, Agent, or Firm* — Dentons US LLP; Lawrence Lavin

(57) ABSTRACT

The present invention relates to compositions and methods for disease control in plants. The compositions for use in the methods of the invention include glyphosate as the active compound. In addition, methods and compositions are disclosed to prevent and treat pest infection in glyphosate tolerant plants.

5 Claims, 2 Drawing Sheets

(56) References Cited

OTHER PUBLICATIONS

Jackson et al.( Influence of Roundup Ready soybean production systems and glyphosate application on pest and beneficial insects in wide-row soybean, Journal of Agricultural and Urban Entomology (2004), 21(2), 61-70 (Year: 2004).*
Response to Non-Final Office Action regarding U.S. Appl. No. 11/638,450, dated Apr. 26, 2016.
USPTO: Final Office Action regarding U.S. Appl. No. 13/319,328, dated Mar. 24, 2016.
Response to Non-Final Office Action regarding U.S. Appl. No. 13/319,328, dated Mar. 2, 2016.
USPTO: Non-Final Office Action regarding U.S. Appl. No. 13/319,328, dated Dec. 2, 2015.
USPTO: Non-Final Office Action regarding U.S. Appl. No. 11/638,450, dated Feb. 25, 2016.
Johal et al., "Glyphosate effects on diseases of plants," *Europ. J. Agronomy* 31:144-152, 2009.
USPTO: Advisory Action regarding U.S. Appl. No. 13/319,328, dated Aug. 27, 2015.
Supplemental Response to Final Office Action regarding U.S. Appl. No. 13/319,328, dated Oct. 6, 2015.
USPTO: Advisory Action regarding U.S. Appl. No. 13/319,328, dated Oct. 22, 2015.
Second Supplemental Response to Final Office Action regarding U.S. Appl. No. 13/319,328, dated Nov. 6, 2015.
Anderson et al., "Rust Control in Glyphosate Tolerant Wheat Following Application of the Herbicide Glyphosate," *Plant Disease*; 89(11); pp. 1136-1142; 2005.
Berner et al. Effects of Glyphosate on Calonectria crotalariae and Red Crown Rot of Soybean; *Plant Dis*; 75:809-813; 1991.
Black et al., Herbicide effects on Rhizoctonia solani in vitro and Rhizoctonia foliar blight of soybean; *Weed Sci*; 44(3); 711-6; 1996.
Bradley et al., "Influence of glyphosate and fungicide coapplications on weed control, spray penetration, soybean response, and yield in glyphosate-resistant soybean," *Agronomy J.*, 100:1360-1365, 2008.
Bradley et al., "Influence of herbicides on Rhizoctonia root and hypocotyl rot of soybean," *Crop Protection*; 21:679-687; 2002.
Brazilian Office Action regarding Patent Application No. PI0509541-7, published May 19, 2015.
Brazilian Office Action regarding Patent Application No. PI0509541-7, published Mar. 26, 2014.
Butzen et al., "Asian Soybean Rust: Fungicide Application Technology," *Crop Insights*, 15(1):1-6, 2005.
European Supplementary Search Report regarding Application No. 05723428.8, dated Oct. 30, 2009.
Feng et al., "Glyphosate inhibits rust diseases in glyphosate-resistant soybeans," *PNAS*; 102(48)17290-17295;2005.
Feng et al., "Disease control activities of glyphosate in glyphosate-resistant crops," *American Chemical Society*, 233rd National Meeting and Exposition, Chicago, IL, Picogram 72:81, Mar. 25-29, 2007.
Feng et al.,"The control of asian rust by glyphosate in glyphosate-resistant soybeans," *PNAS*; 64:353-359;2008.
Final Office Action regarding U.S. Appl. No. 13/319,328, dated May 6, 2015.
Franz et al., "Glyphosate: A unique Global Herbicide"; *Amer Chem Soc*, Chapter 5; pp. 103-141; 1997.
Franz et al., "Toxicology and Environmental Properties of Glyphosate," Glyphosate: A Unique Global Herbicide; *Amer Chem Soc* Monograph 189; pp: 103-142; 1997.
Gardner et al., "Relative fitness of glyphosate-resistant creeping bentgrass lines in Kentucky bluegrass," *HortSci*; 38(3); 455-459; 2003.
Gresshoff et al., "Growth Inhibition by Glyphosate and Reversal of its Action by Phenylalanine and Tyrosine," *Aust. J. Plant Physiol.* 6:177-185, 1979.
Grossbard, "Effects of glyphosate on the microflora; with reference to the decomposition of treated vegetation and interaction with some plant pathogens," Chapter 11 in *The Herbicide Glyphosate*; pp. 159-165, 178-182., 1985.
Han-Ying et al., "Characterization of 5-enolpyruvylshikimate-3-phosphate synthase from sclerotinia sclerotiorum," *Biosciences Information Service*, Zhongguo Shengwu Huaxue yu Fenzi Shengwu Xuebao, 22(4):301-307, 2006. (Abstract).
Lee et al., "Glyphosate and shade effects on glyphosate-resistant soybean defense response to sclerotinia sclerotiorum," *Weed Sci.*, 51(3):294-298, 2003.
Lee et al., "Influence of formulated glyphosate and activator adjuvants on sclerotinia sclerotiorum in glyphosate-resistant and -susceptible glycine max," *Weed Sci.*, 48:710-715, 2000.
Levesque et al., "Effects of glyphosate on *Fusarium* spp.: its influence on root colonization of weeds propagule density in the soil, and crop emergence," *Can. J. Microbiol.*, 33:354-360, 1987.
Njiti et al., "Roundup ready soybean: glyphosate effects on fusarium solani root colonization and sudden death syndrome," *Agronomy J.*, 95(5):1140-1145, 2003.
Non-Final Office Action regarding U.S. Appl. No. 13/319,328, dated Nov. 5, 2014.
Office Action regarding U.S. Appl. No. 11/638,450, dated Jan. 12, 2011.
Powell et al., "A critique of studies evaluating glyphosate effects on diseases associated with *fusarium* spp.," *Weed Res.*, 48(4):307-318, 2008.
Response to Final Office Action regarding U.S. Appl. No. 11/638,450, dated Dec. 5, 2014.
Response to final Office Action regarding U.S. Appl. No. 13/319,328, dated Aug. 5, 2015.
Response to Non-Final Office Action regarding U.S. Appl. No. 11/638,450, dated Apr. 30, 2014.
Response to Non-Final Office Action regarding U.S. Appl. No. 13/319,328, filed Feb. 4, 2015.
Sanogo et al., "Effects of herbicides on *fusarium solani* f. sp. glycines and development of sudden death syndrome in glyphosate-tolerant soybean," *Phytopathology*, 90(1):57-66, 2000.
Sanogo et al., "Field response to glyphosate-tolerant soybean to herbicides and sudden death syndrome," *Plant Disease*, 85(7):773-779, 2001.
Scandiani et al., "Recent Outbreak of Soybean Sudden Death Syndrome Caused by Fusarium virguliforme and F. tucumaniae in Argentina," *Plant Disease Journal* 88:1044 (abstract).
Sprague, "Late-season glyphosate applications in Roundup Ready soybean can be off label," *Crop and Soil Sciences*, ipmnews.msu.edu, Aug. 6, 2009.
Telephonic Interview Summary and Response to Office Action dated Jan. 12, 2011 regarding U.S. Appl. No. 11/638,450, dated Apr. 6, 2011.
Telephonic Interview Summary and Response to Office Action dated Jan. 12, 2011 regarding U.S. Appl. No. 11/638,450.
USPTO: Final Office Action regarding U.S. Appl. No. 11/638,450, dated Sep. 5, 2014.
USPTO: Non Final Office Action regarding U.S. Appl. No. 11/638,450, dated Mar. 27, 2014.
Wyss et al., "Effects of selected herbicides on the germination and infection process of puccinia lagenophora, a biocontrol pathogen of senecio vulgaris," *Biological Control*, 20:160-166, 2001.
Yang et al., "Effects of glyphosate on root diseases in glyphosate-tolerant soybeans," *Phytopathology*, 963:S104, 2003 (Abstract).
Yang, "Soybean (Glycine max) response to glyphosate and soybean cyst nematode (Heterodera glycines)," *Weed Technology*, 16:332-339, 2002.
Zhu et al., "Bioresistance or biodegradation of glyphosate and construction of transgenic plants," *Molecular Plant Breeding*, 1(4):435-441, 2003.
Response to Final Office Action regarding U.S. Appl. No. 13/319,328, dated Aug. 23, 2016.
USPTO: Final Office Action regarding U.S. Appl. No. 11/638,450, dated Sep. 6, 2016.
USPTO: Advisory Action regarding U.S. Appl. No. 13/319,328, dated Sep. 13, 2016.

(56) References Cited

OTHER PUBLICATIONS

Response to Final Office Action regarding U.S. Appl. No. 11/638,450, dated Dec. 6, 2016.
USPTO: Advisory Action regarding U.S. Appl. No. 11/638,450, dated Jan. 12, 2017.
Reply Brief regarding U.S. Appl. No. 13/319,328, dated Nov. 13, 2017.
Morjan et al., "Fungicidal Effects of Glyphosate and Glyphosate Formulations on Four Species of Entomopathogenic Fungi," *Environ. Entomol.* 31(6):1206-1212, 2002.
Njiti et al., "Roundup Ready Soybean: Glyphosate Effects on *Fusarium solani* Root Colonization and Sudden Death Syndrome," *Agron. J.* 95-1140-1145, 2003.
Grossbard et al., "The Action of Gramoxone W. and Roundup on Cereal Pathogens," *Med. Fac. Landbouww. Rijksuniv. Gent.* 41:693-702, 1976.
El-Sayed, "Efficiency of Biocontrol Agents to Control Fusarial Diseases of Watermelon as Influenced by Herbicide Roundup®," *Assiut Journal of Agricultrual Science* 34(2):225-239, 2003.
Jackson et al., "Influence of Roundup Ready® Soybean Production Systems and Glyphosate Application on Pest and Beneficial Insects in Wide-row Soybean," *J. Agric. Urban Entomol.* 21(2):61-70, 2004.
Appeal Brief reguarding U.S. Appl. No. 11/638,450, dated Jun. 5, 2017.
Examiner's Answer Brief regarding U.S. Appl. No. 13/319,328, dated Aug. 11, 2017.
Second Examiner's Answer Brief regarding U.S. Appl. No. 13/319,328, dated Sep. 12, 2017.
Appeal Brief regarding U.S. Appl. No. 13/319,328, dated Apr. 14, 2017.
USPTO: Examiner's Answer Brief regarding U.S. Appl. No. 11/638,450, dated Nov. 27, 2017.
Reply Brief regarding U.S. Appl. No. 11/638,450, dated Jan. 29, 2018.
Patent Trial and Appeal Board Decision on Appeal, regarding U.S. Appl. No. 13/319,328, Appeal No. 2018-001167, dated Jun. 27, 2019.

* cited by examiner

METHODS FOR CONTROLLING PLANT PATHOGENS USING N-PHOSPHONOMETHYLGLYCINE

This application is a divisional of U.S. Ser. No. 11/061,681, which was filed on Feb. 22, 2005, which claims benefit under 35USC § 119(e) of U.S. provisional application Ser. No. 60/557,403, filed Mar. 30, 2004, U.S. provisional application Ser. No. 60/622,134, filed Oct. 26, 2004, and U.S. provisional application Ser. No. 60/654,442, filed Feb. 18, 2005, which are herein incorporated by reference in their entirety.

FIELD OF THE INVENTION

The present invention relates to methods and compositions for pest control in plants. More particularly, it relates to methods and compositions for controlling, preventing, or treating plant pathogens using N-phosphonomethylglycine and compositions containing N-phosphonomethylglycine in plants tolerant to N-phosphonomethylglycine.

BACKGROUND

The development of herbicide tolerant crops allows for the greater use of post-emergent herbicides during agricultural cultivation of the crop. One example of a post-emergent herbicide is N-phosphonomethylglycine, also known as glyphosate, a well known herbicide that has activity on a broad spectrum of plant species. Glyphosate is the active ingredient of Roundup® (Monsanto Co., St. Louis, Mo.), a safe herbicide having a desirably short half-life in the environment. When applied onto a plant surface, glyphosate moves systemically through the plant. Glyphosate is toxic to plants by inhibiting an enzyme in the shikimic acid pathway that provides a precursor for the synthesis of aromatic amino acids. Plants, fungi and some bacteria contain the 5-enolpyruvylshikimate-3-phosphate synthase (EPSPS) enzyme that is sensitive to the toxic effects of glyphosate.

Farmers typically rely on genetic resistance to provide protection from plant pathogen infection and disease. However, sufficient genetic resistance is not always available in the crops being produced or undesirable traits are linked to the genetic resistance genetic loci. Farmers must then apply pesticides to control the pathogen infections, significantly increasing the cost of growing the crops and impact to the environment.

Controlling the crop loss to fungal diseases is expensive. The United States Department of Agriculture estimated that fungicide use to combat the Asian soybean rust alone could add $25 an acre, or 15 percent to 20 percent, to the cost of growing soybeans. If fungicides were applied to all U.S. fields planted with soybeans in 2004, it would cost farmers a total of about $1.87 billion.

It would be advantageous to develop methods and chemical mixtures for controlling pathogens and disease in glyphosate tolerant crop plants using compositions that are effective and safe. Such methods would reduce the cost of growing crops by reducing the number of inputs a farmer uses to treat a crop field while providing protection from losses do to plant disease.

SUMMARY OF THE INVENTION

The present invention provides a method of controlling plant pathogen disease in a glyphosate tolerant crop plant where the method comprises, identifying a crop plant in need of disease control, and contacting the plant with an effective amount of a composition having glyphosate, whereby the disease of the crop plant by a plant pathogen is controlled. In particular, the plant pathogen is a fungus and has a glyphosate sensitive 5-enolpyruvylshikimate-3-phosphate synthase.

The present invention also provides a method of preventing disease in a glyphosate tolerant crop plant by a pathogen where the method comprises, identifying a crop plant at risk of pathogen infection, and contacting at least a portion of the crop plant with an effective amount of glyphosate to prevent infection of the plant by a plant pathogen. In particular, the plant pathogen is a fungus and has a glyphosate sensitive 5-enolpyruvylshikimate-3-phosphate synthase.

The present invention further provides a method of treating a plant disease that comprises, identifying a glyphosate tolerant crop plant infected with a plant pathogen, and contacting the crop plant with an effective amount of a composition comprising glyphosate. In particular, the plant pathogen is a fungus and has a glyphosate sensitive 5-enolpyruvylshikimate-3-phosphate synthase.

The present invention also provides a method of controlling weeds and pathogens in a field of glyphosate tolerant crop plants, where the method comprises applying a first composition comprising an herbicidal composition, and applying a second composition comprising an effective amount of glyphosate, where the second composition controls a disease of the crop plants by a plant pathogen that has a glyphosate sensitive 5-enolpyruvylshikimate-3-phosphate synthase.

The present invention further provides a method of increasing the yield of a glyphosate tolerant crop plant, the method comprising, growing a crop plant having an exogenous nucleic acid molecule encoding a polypeptide, where the polypeptide confers tolerance to glyphosate, identifying said crop plant as in need of disease control, applying a composition comprising glyphosate to the plant to control a plant pathogen that has a glyphosate sensitive 5-enolpyruvylshikimate-3-phosphate synthase, and harvesting from the crop plant a tissue or seed, wherein the yield increase is due to control of the disease.

The present invention also provides an admixture of a glyphosate compound and a pest control compound. Preferably, the admixture comprises a glyphosate compound and a fungicide compound for use on a glyphosate tolerant cro plant to prevent or control plant disease caused by a plant pathogen, in particular, the plant pathogen is a fungus and has a glyphosate sensitive 5-enolpyruvylshikimate-3-phosphate synthase. The fungicide compound of the admixture may be a systemic or contact fungicide or mixtures of each. More particularly the fungicide compound includes, but is not limited to members of the chemical groups strobilurins, triazoles, chloronitriles, carboxamides and mixtures thereof. The pest control compound in the admixture with glyphosate further comprises an insecticide compound, thereby reducing the numbers of chemical applications to a field of glyphosate tolerant plants.

The present invention provides a method to reduce the crop residues and environmental residues of a glyphosate compound and a fungicide compound by formulating an admixture of the compounds, and applying to a crop plant a dose that is less than the dose normally applied to a crop plant of each compound, wherein the treated crop plant is protected from crop losses due to fungal disease, and the glyphosate and fungicide residues in the plant or environment are reduced.

The present invention also provides a method to reduce fungal resistance to a fungicide by providing an admixture of a glyphosate compound and a fungicide compound, and treating a crop plant that is susceptible to a fungal pathogen, wherein the compounds have different modes of action to prevent or reduce fungal disease.

The present invention also provides a method for treating leaf rust in a soybean plant comprising identifying a soybean plant as being infected with rust, and applying a composition having glyphosate to the soybean plant or portion thereof, whereby the composition results in the disease being controlled. In another aspect the treatment is a composition having a glyphosate and a fungicide composition to the soybean plant or portion thereof, whereby the composition results in the disease being controlled.

The present invention also provides a method for preventing leaf rust in a soybean plant comprising identifying a soybean plant as being at risk of infection by rust, and applying a composition having glyphosate to the soybean plant or portion thereof, whereby the infection is inhibited in the soybean plant. In another aspect of the invention, a composition having a glyphosate compound and a fungicide compound is applied to the soybean plant or portion thereof, whereby the infection is inhibited in the soybean plant.

The present invention also provides a method for treating leaf rust in a corn plant comprising identifying a corn plant as being infected with rust, and applying a composition having glyphosate to the corn plant or portion thereof, whereby the composition results in the disease being controlled.

The present invention also provides a method for treating leaf rust in a corn plant comprising identifying a corn plant as being infected with rust, and applying a composition having a glyphosate compound and a fungicide compound to the corn plant or portion thereof, whereby the composition results in the disease being controlled.

The present invention also provides a method for preventing leaf rust in a corn plant comprising identifying a corn plant as being at risk of infection by rust, and applying a composition having glyphosate to the corn plant, whereby the infection is inhibited in the corn plant.

The present invention also provides a method for preventing leaf rust in a corn plant comprising identifying a corn plant as being at risk of infection by rust, and applying a composition having a glyphosate compound and a fungicide compound to the corn plant, whereby the infection is inhibited in the corn plant.

The present invention also provides a method for treating a fungal wilt disease in a cotton plant comprising identifying a cotton plant as being infected with the fungal wilt pathogen, and applying a composition having glyphosate to the cotton plant or portion thereof, whereby the composition results in the disease being controlled. In another aspect of the method, the glyphosate composition comprises a plant systemic fungicide.

The present invention also provides a method for preventing a fungal wilt disease in a cotton plant comprising identifying a cotton plant as being at risk of infection by a fungal wilt pathogen, and applying a composition having glyphosate to the cotton plant, whereby the infection is inhibited in the cotton plant. In another aspect of the method, the glyphosate composition comprises a plant systemic fungicide.

The present invention also contemplates a glyphosate containing composition that is enhanced for the uptake into glyphosate tolerant crops or fungal pathogens of those crops. In another aspect of the present invention, the glyphosate composition comprises an adjuvant.

A method to control a fungal disease in a glyphosate tolerant crop plant comprising treatment of the crop plant with an effective dose of a glyphosate composition, wherein the crop plant is selected from the group consisting of Roundup Ready® Cotton 1445 and 88913; Roundup Ready® corn GA21, nk603, MON802, MON809; Roundup Ready® Sugarbeet GTSB77 and H7-1; Roundup Ready® Canola RT73 and GT200; oilseed rape ZSR500, Roundup Ready® Soybean 40-3-2, Roundup Ready® Bentgrass ASR368, and Roundup Ready® potato RBMT22-082. Preferably, the glyphosate composition is in a formulation comprising Roundup WeatherMAX®, more preferably the glyphosate composition contains a fungicide.

A method for controlling a fungal disease in a glyphosate tolerant crop plant comprising treatment of a crop plant cell with a glyphosate composition, wherein a chemical exchange between the crop plant cell and a fungal cell occurs allowing movement of the glyphosate into the fungal cell from the crop plant cell, and the fungal cell contains a glyphosate sensitive EPSPS enzyme. In another aspect of the method, the glyphosate composition comprises a plant systemic fungicide.

The present invention also provides a container comprises a glyphosate compound and a pest control compound. In another aspect of the invention, a kit is provided for controlling pathogens on crop plants, comprising, a composition comprising glyphosate, and an instruction means for applying the composition in a first application to control weeds and a second application to a crop plant to control a plant pathogen. In particular, the plant pathogen is a fungus and has a glyphosate sensitive 5-enolpyruvylshikimate-3-phosphate synthase.

DETAILED DESCRIPTION

Figure 1:
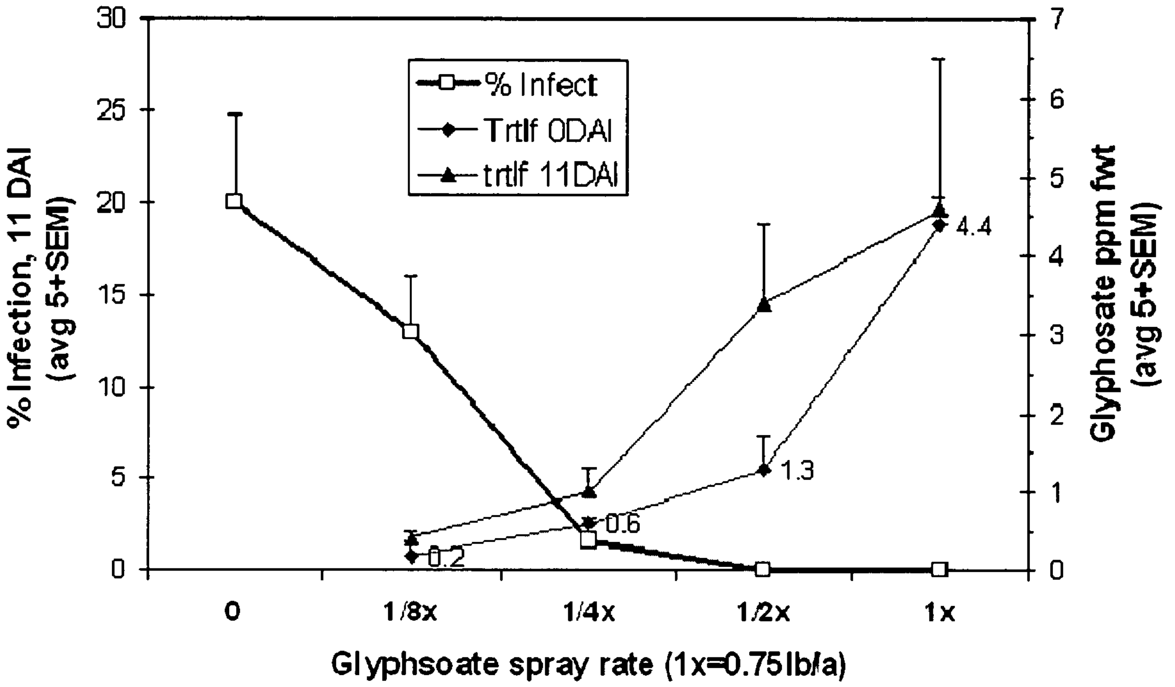
FIG. 1 is a graph depicting a decrease in rust disease infection with an increase in glyphosate treatment. In the data shown in FIG. 1, the top fully expanded wheat leaf was shielded from Roundup® spray (0-1×, 1× at 0.75 lb ae/a) followed by inoculation of wheat rust spores to the shielded leaf at 1 day after treatment (DAT).

The present invention relates to methods and compositions for disease control, prevention or treatment in plants. In a preferred aspect, the methods of the invention relate to methods of controlling, preventing or treating disease in glyphosate tolerant crop plants.

Typically, glyphosate compositions have been applied as an herbicide. Surprisingly, it has been found that glyphosate compositions also have pesticidal properties. In a preferred aspect, the glyphosate compositions have fungicidal activity when used on glyphosate tolerant crop plants. In another aspect of the invention, a composition that comprises a glyphosate compound and a fungicide compound has been shown to be particularly effective in controlling fungal disease. A reduced dosage rate of each compound than that normally applied to control weeds or fungal disease has been shown to be effective in controlling fungal disease.

As such, the present invention provides methods of using glyphosate compositions or admixtures containing glyphosate and a fungicide for controlling, preventing or treating plant pathogen infection in glyphosate tolerant crop plants. These methods are useful in the control, prevention or treatment of plant disease, for example, fungal diseases in soybean, wheat, corn, rice, canola, alfalfa, sugarbeet, potato, tomato, cotton or other crop plants genetically modified for glyphosate tolerance.

The section headings are used herein for organizational purposes only, and are not to be construed as in any way limiting the subject matter described.

I. Methods of the Present Invention

The present disclosure provides methods for controlling, preventing or treating disease in crop plants by applying compositions containing N-phosphonomethylglycine and the salts thereof (also referred to herein as glyphosate compound) to a crop plant in need of disease control, prevention or treatment. In one aspect, the methods include contacting a crop plant in need of disease control, prevention or treatment with an effective amount of a chemical composition containing glyphosate to control, prevent or treat a plant pathogen infection in the crop plant. In a preferred aspect, the crop plant for which disease control, prevention or treatment is desired is glyphosate tolerant.

As used herein "disease control" refers to preventing or treating a pathogen infection in a plant. It is intended that the plants avoid or minimize the disease or symptoms thereof that are the outcome of various plant-pathogen interactions. That is, pathogens are prevented from causing plant diseases or the associated disease symptoms or both, or alternatively, the disease or associated disease symptoms are minimized or lessened in plants treated with a glyphosate composition compared to an untreated plant. In a preferred aspect, infection is prevented or controlled through glyphosate activity on the pathogen. While the invention does not depend on any particular reduction in the severity of disease symptoms, the methods of the invention will in one aspect reduce the disease symptoms resulting from a pathogen infection by at least about 5%, 10%, 20%, 30%, 40%, 50%, 60%, 70%, 80%, 90%, 95% compared to a plant not treated with a glyphosate composition (or an "untreated plant"). Hence, the methods of the invention include those that can be utilized to protect plants from disease, particularly those diseases that are caused by plant pathogens. A reduction in infection or disease symptoms can be measured using any reproducible means of measurement. In one aspect, a reduction in infection or disease symptoms is measured by counting the number of lesions, pustules, or both on a leaf surface and comparing to the number of lesions, pustules or both on an untreated plant.

As used herein, a "plant in need" refers to any plant for which disease control, prevention or treatment is desired. In particular, the term refers to a plant that is at risk of being infected by a plant pathogen, or is infected by a pathogen. A plant may be at risk of infection in circumstances where pathogens are more likely to infect the plant, for example, in disease optimal climate conditions or where other disease hosts in a field have been treated with a herbicide and disease crossover from the dying plant to the standing plant is possible. An infected plant can be identified through observation of disease symptoms on the plant. The disease symptoms expressed will depend on the disease, but in general the symptoms include lesions, pustules, necrosis, hypersensitive responses, wilt, chlorosis, induction of defense related genes (e.g. SAR genes) and the like.

Disease infections or associated symptoms can be identified by any means of identifying infection or related symptoms. Various methods are available to identify infected plants and the associated disease symptoms. In one aspect, the methods may involve macroscopic or microscopic screening for infection and/or symptoms, or the use of microarrays for detection of infection related genes (e.g. Systemic Acquired Resistance genes, defensin genes, and the like). Macroscopic and microscopic methods for determining pathogen infection in a plant are known in the art and include the identification of damage on plant tissue caused by infection or by the presence of lesions, necrosis, spores, hyphae, growth of fungal mycelium, wilts, blights, spots on fruits, rots, galls and stunts, and the like. Such symptoms can be compared to non-infected plants, photos or illustrations of infected plants or combinations thereof to determine the presence of an infection or the identity of the pathogen or both. Photos and illustrations of the symptoms of pathogen infection are widely available in the art and are available for example, from the American Phytopathological society, St. Paul, Minn. 55121-2097. In one aspect, the symptoms are visible to the naked eye or by a specified magnification. In a preferred aspect, the specified magnification is 2×, 3×, 4×, 5×, 10×, or 50×.

In another aspect, the infection or associated symptom can be identified using commercially available test kits to identify pathogens in plants. Such test kits are available, for example, from local agricultural extensions or cooperatives. In another aspect, identifying a crop plant in need of treatment is by prediction of weather and environmental conditions conducive for disease development. In another aspect, persons skilled in scouting fields of crop plants for plant disease identify a crop in need of treatment.

In yet another aspect, an infection or associated symptom can be identified using Polymerase chain reaction (PCR)-based diagnostic assays. PCR-based assays are described for example to detect the presence of *Gaeumannomyces graminis* (GGT, Take-all disease) in infected wheat using PCR amplification of sequences specific to the pathogen mitochondrial genome (Schlesser et al., 1991; Applied and Environ. Microbiol. 57: 553-556), and random amplified polymorphic DNA (i.e. RAPD) markers to distinguish numerous races of *Gremmeniella abietina*, the causal agent of scleroderris canker in conifers. U.S. Pat. No. 5,585,238 (incorporated by reference in its entirety) describes primers derived from the ITS sequences of the ribosomal RNA gene region of strains of *Septoria, Pseudocercosporella*, and *Mycosphaerella* and their use in the identification of these fungal isolates using PCR-based techniques. In addition, U.S. Pat. No. 5,955,274 (incorporated by reference in its entirety) describes primers derived from the ITS sequences of the ribosomal RNA gene region of strains of *Fusarium* and their use in the identification of these fungal isolates using PCR-based techniques. Furthermore, U.S. Pat. No. 5,800,997 (incorporated by reference in its entirety) describes primers derived from the ITS sequences of the ribosomal RNA gene region of strains of *Cercospora, Helminthosporium, Kabatiella*, and *Puccinia* and their use in the identification of these fungal isolates using PCR-based techniques. The specific methods of identification will depend on the pathogen.

As used herein, "contacting" refers to treatment of a crop plant with a glyphosate composition either directly on a crop plant, or immediately adjacent to the crop plant where the glyphosate can be taken-up into the crop plant's vascular system. In methods where the composition is directly contacted with the crop plant, the composition may be contacted with the entire crop plant or with only a portion of the plant. Additionally, a plant pathogen may be contacted with the glyphosate composition either by direct contact on a plant surface or by contacting a plant cell or tissue that contains glyphosate. In a preferred aspect, a plant is contacted with a glyphosate composition by overhead spraying of the composition.

The term "effective amount" means an amount of the glyphosate compound sufficient to result in any observable measure of disease control, prevention or treatment in a plant. Preferably, an effective amount of glyphosate results in a concentration of glyphosate in a plant tissue of between about 0.01 parts per million (ppm) to about 100 ppm per fresh weight. More preferable, tissue concentrations of between 0.1 ppm and 25 ppm glyphosate of fresh weight are obtained in the tissues of plants treated in the methods of the present invention. Most preferably, tissue concentrations of between about 0.5 ppm and about 10 ppm glyphosate are effective in controlling, preventing or treating disease in a treated plant.

Effective rates of application in the present invention for a glyphosate compound can be influenced by many factors including the environment and should be determined under actual use conditions. Preferably, the disease control, prevention or treatment is obtained with an application of glyphosate at a rate similar to or less than the amount used for weed control. More preferably, a rate of application of a glyphosate compound from about 0.1 pounds acid equivalent/acre (lb ae/acre, herein referred to lb/acre) to about 5 lb/acre of glyphosate is effective in controlling, preventing or treating a pathogen in accordance with the method of the present invention. Yet more preferable are rates of application ranging from about 0.37 lb/acre to about 2.5 lb/acre. Most preferable are rates of application of about 0.75 lb/acre, herein referred to as 1× glyphosate rate.

In a preferred aspect plant disease control, prevention or treatment is accomplished by applying an effective amount of a glyphosate composition either pre- or post-infection, to the whole plant or a portion of the plant such as the roots, stems, foliage, fruit, seeds, tubers or bulbs, or to the media (e.g., soil, sand or water) in which the plants to be protected are growing. In one aspect, a glyphosate is translocated through the vascular system in plants and therefor the entire plant is not required to be contacted. Thus, in one aspect a portion of a plant may be treated with a glyphosate composition, and a disease controlled, prevented or treated in the treated portion as well as in untreated portions of the plant, such as untreated leaves, stems, or roots. In one particular aspect, untreated leaves of glyphosate tolerant wheat plants have decreased disease infection when lower leaves are treated with a composition containing glyphosate. In a particularly preferred aspect, disease control, prevention or treatment corresponds to the concentration of glyphosate in the tissue of the untreated leaf. In another aspect, a glyphosate composition can also be applied to the seed to protect the seed and seedling.

As used herein, "pre-infection" refers to a condition in which a plant has not been exposed to a plant pathogen or a material contaminated with a plant pathogen.

The term "post-infection" refers to a condition where a plant has been exposed to a plant pathogen or a material contaminated with a plant pathogen. The plant may or may not be showing symptoms of the infection. For example, the plant may be infected with a pathogen yet not showing signs of the infection, e.g., a hypersensitive response (HR).

Preferably, the methods of the present invention control, prevent or treat disease in a plant through the direct action of the glyphosate composition on the plant pathogen. Disease control, prevention or treatment may also be, in part, the result of systemic acquired resistance (SAR) induced by the application of the glyphosate composition. In a preferred aspect, the disease control, prevention or treatment obtained by the methods of the present invention is the result of the direct action of the glyphosate and not the result of induced SAR.

By "glyphosate tolerant" is meant that the plants for use in the methods are resistant to glyphosate application or tolerant of glyphosate. In a preferred aspect of the present invention glyphosate tolerant plants are the result of the expression of an exogenous nucleic acid molecule providing tolerance to glyphosate.

As such, the present invention provides methods of preventing disease in a plant by applying an effective amount of a glyphosate composition to a plant, such that infection of a plant by a pathogen is prevented. In one preferred aspect, the plant for use in the methods is glyphosate tolerant.

By "preventing infection" is intended that the plants avoid pathogen infection or disease symptoms or both, or exhibit reduced or minimized pathogen infection or disease symptoms or both, that are the natural outcome of plant-pathogen interactions when compared to plants lacking treatment with glyphosate compositions (or "untreated plants"). That is, pathogens are prevented or reduced from causing disease, the associated disease symptoms or both. The methods of the invention can be utilized to protect plants from disease, particularly those diseases that are caused by fungal plant pathogens.

By preventing or reducing pathogen infection or the related disease symptoms, the infection or symptoms or both are preferably reduced at least about 10% from a plant untreated by a glyphosate composition. Preferably, the infection, symptoms or both are prevented or reduced at least about 20%, 30%, 40%, 50%, 60%, 70%, 80% compared to infection, symptoms or both on a plant not treated with a glyphosate composition. Disease infection may be measured by any reproducible means of measurement. In one aspect, infection may be measured by counting lesions or pustules visible to the naked eye, or at a specified magnification. In a preferred aspect, the specified magnification is 2×, 3×, 4×, 5×, 10×, or 50×.

In a preferred aspect, the methods of the present invention provide for disease prevention for a period of time after treatment with a glyphosate composition. Preferably, the glyphosate composition prevents severe disease of the plant for several weeks after application of the glyphosate composition. More preferably, disease is prevented at least about 14, 15, 16, 17, 18, 19, 20, 21, 22, 23, 24, 25, 26, 27, 28, 29, 30, 35 days after treatment with a glyphosate composition. In one especially preferred aspect, disease is prevented for at least about 40 days after treatment of the plant with a glyphosate composition. Prevention of disease may be measured by any reproducible means of measurement. In a preferred aspect, disease prevention is measured by counting lesion or pustule development at time points after treatment with a glyphosate composition. In a preferred aspect, the lesions or pustules are counted 7, 8, 9, 10, 11, 12, 13, 14, 15, 16, 17, 18, 19, 20, 25, 30 days after glyphosate treatment.

As discussed more fully below, depending on the method employed for conferring glyphosate tolerance or resistance, application of glyphosate may prevent infection or disease for shorter or longer periods of time after treatment. For example, where glyphosate tolerance is imparted to a plant by an exogenous DNA encoding a polypeptide that degrades glyphosate (e.g. glyphosate oxidoreductase or glyphosate acetyl transferase), disease will be prevented for a shorter period of time compared to a glyphosate tolerance imparted by the expression of an exogenous polypeptide that is less inhibited by glyphosate (e.g. a modified EPSPS) allowing glyphosate conservation in plant tissues. Glyphosate tolerance in plants can be achieved by the expression of a modified class I EPSPS that has lower affinity for glyphosate, however, still retains their catalytic activity in the presence of glyphosate (U.S. Pat. Nos. 4,535,060, and 6,040,497 (both of which are incorporated by reference in their entirety)). EPSPS enzymes, such as, class II EPSPSs have been isolated from bacteria that are naturally resistant to glyphosate and when the enzyme is expressed as a gene product of a transgene in plants provides glyphosate tolerance to the plants (U.S. Pat. Nos. 5,633,435 and 5,094,945 (both of which are incorporated by reference in their entirety)). The present invention contemplates the use of any EPSPS enzyme, modified or naturally occurring, for example, glyphosate resistant EPSPS enzymes isolated from microbial sources that are not Class I or Class II enzymes, and modified Class I EPSPSs (WO04/07443 (incorporated by reference in its entirety)), that have resistance to glyphosate for use as a transgene in a transgenic plant. Such enzymes are known to those skilled in the art of making glyphosate tolerant plants.

In another aspect, application of a glyphosate composition is effective in preventing disease or the associated symptoms at a site on the plant distant from the point at which the glyphosate compositions are applied. In one aspect, foliar application of the glyphosate compositions is effective in preventing pathogens from colonizing relatively distant and inaccessible regions of the plant, such as the roots and meristems. In another aspect, disease prevention in leaves of a plant is obtained through contacting the medium in which the plant is growing. This remote effect occurs because the glyphosate compounds are transported in the plant vascular system, which allows for long distance transport of the compounds within living plants. In addition, disease prevention may be enhanced by application of the glyphosate formulations through induction of systemic acquired resistance (SAR). SAR occurs in plants in response to infection, particularly by necrotizing pathogens, or induced by certain compounds, and provides enhanced resistance to subsequent attacks by the same or even unrelated pathogens. SAR provides longterm (weeks to months) protection throughout the plant (systemic) against a broad range of unrelated pathogens. Examples of defense responses induced in plant cells include the synthesis of plant cell structural components such as cutin suberin, callose and lignin, chemical defense compounds such as hydrogen peroxide, and anti-bacterial or anti-fungal compounds such as tannins and phytoalexins. In a preferred aspect, disease is prevented in a plant primarily through the direction action of glyphosate rather than through induction of SAR.

Thus, methods of preventing disease in a plant are provided where only a portion of the plant is contacted with a glyphosate composition, yet untreated portions of the plant are also protected from disease. In one aspect, only about 5%, 10%, 20%, 30%, 50%, 75% or 90% of the plant is contacted with the glyphosate composition. The percentage of plant contacted by the glyphosate composition may be measured by any reproducible means of measurement.

One aspect of the present invention provides a method for the prevention of infection in a soybean, corn, rice, cotton, alfalfa, sugarbeet, or wheat plant. The method generally involves applying an effective amount of a glyphosate composition to a soybean, corn, rice, cotton, alfalfa, sugarbeet or wheat plant, or part thereof to prevent infection of the plant. In one preferred aspect, the soybean, corn, rice, cotton, alfalfa, sugarbeet, or wheat plants are glyphosate tolerant. One particularly preferred aspect provides methods for preventing the infection of soybean, corn, cotton, or wheat plants by fungal pathogens. In a preferred aspect methods for preventing infection by leaf rust on corn, wheat and soybeans are provided. In another preferred aspect methods for preventing infection and fungal wilt disease of cotton is provided.

In another aspect, the methods of the present invention provide for controlling, preventing or treating rust disease (*Phakopsora pachyrhizi*) in soybean plants by application of glyphosate compositions to a soybean plant in need of disease control, prevention or treatment. In a preferred aspect, the soybean is glyphosate tolerant.

Also provided are methods of treating a plant disease by identifying a plant infected by a plant pathogen (i.e. post-infection) and contacting the infected plant with an effective amount of a glyphosate composition such that the infection is treated. In a preferred aspect, the infected plant is glyphosate tolerant. Infection can be measured by any reproducible means of measurement. In one aspect, infection is measured by counting the number of lesions visible to the naked eye, or at a specified magnification. In a preferred aspect, the specified magnification is 2×, 3×, 4×, 5×, 10× or 50×.

By "treating" a plant disease is meant that the symptoms caused by the plant pathogen are reduced or do not progress in severity. A reduction in severity means that the surface area of the leaf exhibits less infection or reduced symptoms (e.g., by percentage of leaf surface) on the treated plant at a time after treatment compared to symptoms at the time of treatment. In one aspect, infection is reduced 5%, 10%, 25%, 50%, or 75% compared to an infected plant not treated with a glyphosate composition.

In another aspect, lesions are prevented from increasing in size or progressing to the next level of infection or symptom. In a preferred aspect, the lesions are reduced from progressing to pustules. In one aspect, 10%, 20%, 30%, 40%, 50%, 60%, 70%, 80%, 90%, 95%, 99% of the lesions are prevented from becoming pustules on the leaf surface. Lesion development may be measured by any reproducible means of measurement. In one aspect, lesion development may be measured by comparing the number of visible pustules on a plant surface at a time after treatment with the number of visible lesions on the plant surface at the time of treatment with a glyphosate composition.

In addition, methods for treating infection of a plant by a plant pathogen are provided wherein a non-infected portion of the plant is treated with glyphosate. Such methods include determining that the plant is infected with a plant pathogen, then applying a composition containing glyphosate to a portion of the plant that is not infected with the pathogen. Application of the glyphosate composition to the non-infected area of the plant results in the treatment of infection at another location on the plant.

The present invention also provides methods for controlling harmful weeds and controlling, preventing or treating pathogens in a field of glyphosate tolerant crop plants where the method uses applications of glyphosate compositions. Such methods comprise one or more applications of a glyphosate composition to a field of crop plants tolerant or resistant to glyphosate, preferably two or more applications. Preferably, the application or applications are timed for effective weed control and effective disease control, prevention or treatment in the treated plant. For example, without limitation, a first application of glyphosate is applied at a time when the application controls the weeds within the field of plants. For example, without limitation, a second application is at a time when the crop plants are either at risk of infection or have already been infected by a plant pathogen. In one aspect, the application of a glyphosate composition results in a concentration of glyphosate in a plant tissue of between about 0.01 ppm to about 100 ppm per fresh weight. More preferable, tissue concentrations of between 0.1 ppm and 25 ppm glyphosate of fresh weight are obtained in the tissues of plants treated in the methods of the present invention. Most preferably, concentrations of between about 0.5 ppm and about 10 ppm glyphosate are effective in controlling, preventing or treating disease in a treated plant.

Effective rates of application in the present invention for a glyphosate composition can be influenced by many factors including the environment and should be determined under actual use conditions. Preferably, the rate of application of a glyphosate composition from about 0.1 lb/acre to about 5 lb/acre of glyphosate is effective in controlling, preventing or treating a pathogen in accordance with a method of the present invention. Yet more preferable are rates of application ranging from about 0.37 lb/acre to about 2.5 lb/acre. Most preferable are rates of application of about 0.75 lb/acre.

In one aspect, methods for controlling weeds and pathogens in a field crop comprises the steps of (a) planting a crop in a field, (b) substantially freeing the field of non-crop plants by applying an herbicidal composition and (c) thereafter control, prevent or treat disease by applying a glyphosate composition. In such a method, it should be appreciated that the steps of planting and substantially freeing can be interchanged. Thus, the field may be substantially free of non-crop plants before planting the crop in the field. In one aspect, the application of the herbicidal composition and the disease control glyphosate application are 1 day apart, 2, 3, 4, 5, 6, 7, 8, 9, 10, 14, 21 days apart. In another aspect, the herbicidal and pesticidal applications are greater than 5, 10, 20, 25, 30, 35, 40, 45, or 50 days apart.

In one aspect, the glyphosate composition is applied one or more times during the growing season. In another aspect, the glyphosate composition is applied 2, 3, 4, 5, 6, 7, 8, 9, 10 times during the growing season to a plant in need of disease control, prevention or treatment.

The present invention also provides methods for increasing the yield of a plant, by growing a plant having an exogenous nucleic acid molecule encoding a polypeptide, where the polypeptide confers resistance to glyphosate, determining the plant is infected or is at risk of being infected with a plant pathogen, applying a composition comprising (comprising means "including but not limited to) glyphosate to the plant to control, prevent or treat a plant pathogen, and harvesting from the plant a tissue. In a preferred aspect, such methods increase the yield of plant tissues including, but not limited to: seeds, fruits, kernels, bolls, tubers, roots, and leaves. In an aspect of the present invention, the yield is increased 5%, 10%, 15%, 20%, 25%, 30%, 50% compared to plants not treated with a glyphosate composition for disease control, prevention or treatment. In a preferred aspect, the increase in yield is measured relative to the dry weight of a seed or an average in the increase in dry weight across a collection of seeds. In a preferred aspect of the present invention a collection of seeds is all, or a percentage of all, for example 25%, 50% or 75%, of the seeds on an individual plant, a representative number of seeds from a field or planting area subject to a method of the present invention or in the case of a comparison not subject to a method of the present invention. In a preferred aspect, the representative number of seeds selected is sufficient for a statistical analysis.

The present invention also provides a kit for the control, prevention or treatment of plant disease, where the kit comprises a container having a glyphosate composition and instructional material for applying the glyphosate composition to control, prevent or treat a plant pathogen infection in accordance with a method of the present invention. The skilled artisan will appreciate that the instructions for applying the glyphosate composition in the methods of the present invention can be any form of instruction means. Such instructions include, but are not limited to, written instruction material (such as, a label, a booklet, a pamphlet), oral instructional material (such as on an audio cassette or CD) or video instructions (such as on a video tape or DVD).

II. Glyphosate Compositions

The compositions for use in the methods of the present invention include compositions having as their effective ingredient N-phosphonomethylglycine, also referred to herein as glyphosate. Thus, the compositions for use in the methods of the present invention include any composition containing a glyphosate compound. In particular, compositions containing a glyphosate compound and a fungicide compound are additive or synergistic in activity against susceptible fungal pathogens. Glyphosate is an effective broad spectrum herbicide. Various methods are known for producing glyphosate, as shown, for example, in U.S. Pat. Nos. 3,927,080; 3,956,370; 3,969,398; 4,147,719; and 4,654,429 (all of which are incorporated by reference in their entirety). As used herein, "glyphosate" refers to N-phosphonomethylglycine, a salt or ester thereof, or a compound which is converted to glyphosate in plant tissues or which otherwise provides glyphosate ion. This includes the TMS salt of glyphosate (commercially available under the trade Touchdown™), as well as sulfosate and its salts. In one aspect glyphosate, glyphosate salts or both that are useful in a method of the present invention are disclosed in U.S. Pat. No. 3,799,758, herein incorporated by reference in its entirety. In another aspect many derivatives of N-phosphonomethylglycine will exhibit broad spectrum pesticidal activity, and thus any such pesticidal derivatives will be defined as glyphosate for the purposes of the present invention. In another aspect, any formulation of glyphosate is within the scope of the present invention. In one preferred aspect, the glyphosate composition comprises salts of the cationic and anionic form of glyphosate, more preferably, the anionic form of glyphosate The chosen glyphosate composition is preferably applied to the plants to be protected or treated in the form of a composition with further carriers, surfactants, adjuvants or other application-promoting chemicals customarily employed in formulation technology. Suitable carriers, surfactants, and adjuvants can be solid or liquid and are the substances ordinarily employed in formulation technology, for example, natural or regenerated mineral substances, solvents, dispersants, wetting agents, tackifiers, thickeners, binders or fertilizers.

A preferred method of applying a glyphosate composition is application to the parts of the plants that are above the soil, especially to the leaves (foliar application). The frequency and rate of application depend upon the biological and climatic living conditions of the pathogen. The composition can, however, also penetrate the plant through the roots via the soil or via the water (systemic action) if the locus of the plant is impregnated with a liquid formulation (e.g. in rice culture) or if the composition is introduced in solid form into the soil, e.g. in the form of granules (soil application). In order to treat seed, the composition can also be applied to the seeds (coating), either by impregnating the tubers or grains with a liquid formulation of the composition, or by coating them with an already combined wet or dry formulation. In addition, in special cases, other methods of application to plants are possible, for example treatment directed at the buds or the fruit trusses.

The glyphosate compositions used in the methods of the present invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, azinphos-methyl, bifenthrin, buprofezin, carbofuran, chlorfenapyr, chlorpyrifos, chlorpyrifos-methyl, cyfluthrin, beta-cyfluthrin, cyhalothrin, lambda-cyhalothrin, deltamethrin, diafenthiuron, diazinon, diflubenzuron, dimethoate, esfenvalerate, fenoxycarb, fenpropathrin, fenvalerate, fipronil, flucythrinate, tau-fluvalinate, fonophos, imidacloprid, isofenphos, malathion, metaldehyde, methamidophos, methidathion, methomyl, methoprene, methoxychlor, methyl 7-chloro-2,5-dihydro-2-[[N-(methoxycarbonyl)-N-[4-(trifluoromethoxy)phenyl]amino]carbonyl]indeno-[1,2-e][1,3,4]oxadiazine-4a(3H)-carboxylate (DPX-JW062), monocrotophos, oxamyl, parathion, parathion-methyl, permethrin, phorate, phosalone, phosmet, phosphamidon, pirimicarb, profenofos, rotenone, sulprofos, tebufenozide, tefluthrin, terbufos, tetrachlorvinphos, thiodicarb, tralomethrin, trichlorfon and triflumuron; most preferably a glyphosate compound is formulated with a fungicide compound or combinations of fungicides, such as azoxystrobin, benomyl, blasticidin-S, Bordeaux mixture (tribasic copper sulfate), bromuconazole, captafol, captan, carbendazim, chloroneb, chlorothalonil, copper oxychloride, copper salts, cymoxanil, cyproconazole, cyprodinil (CGA 219417), diclomezine, dicloran, difenoconazole, dimethomorph, diniconazole, diniconazole-M, dodine, edifenphos, epoxiconazole (BAS 480F), famoxadone, fenarimol, fenbuconazole, fenpiclonil, fenpropidin, fenpropimorph, fluazinam, fluquinconazole, flusilazole, flutolanil, flutriafol, folpet, fosetyl-aluminum, furalaxyl, hexaconazole, ipconazole, iprobenfos, iprodione, isoprothiolane, kasugamycin, kresoxim-methyl, mancozeb, maneb, mepronil, metalaxyl, metconazole, S-methyl 7-benzothiazolecarbothioate (CGA 245704), myclobutanil, neo-asozin (ferric methanearsonate), oxadixyl, penconazole, pencycuron, probenazole, prochloraz, propiconazole, pyrifenox, pyroquilon, quinoxyfen, spiroxamine (KWG4168), sulfur, tebuconazole, tetraconazole, thiabendazole, thiophanate-methyl, thiram, triadimefon, triadimenol, tricyclazole, trifloxystrobin, triticonazole, validamycin and vinclozolin; combinations of fungicides are common for example, cyproconazole and azoxystrobin, difenoconazole, and metalaxyl-M, fludioxonil and metalaxyl-M, mancozeb and metalaxyl-M, copper hydroxide and metalaxyl-M, cyprodinil and fludioxonil, cyproconazole and propiconazole; commercially available fungicide formulations for control of Asian soybean rust disease include, but are not limited to Quadris® (Syngenta Corp.), Bravo® (Syngenta Corp), Echo 720® (Sipcam Agro Inc), Headline® 2.09EC (BASF Corp.), Tilt® 3.6EC (Syngenta Corp), PropiMax™ 3.6EC (Dow AgroSciences), Bumper® 41.8EC (Makhteshim-Agan), Folicur® 3.6F (Bayer CropScience), Laredo® 25EC (Dow AgroSciences), Laredo™ 25EW (Dow AgroSciences), Stratego® 2.08F (Bayer Corp), Domark™ 125SL (Sipcam Agro USA), and Pristine®38% WDG (BASF Corp) these can be combined with glyphosate compositions as described in the present invention to provide enhanced protection from soybean rust disease; nematocides such as aldoxycarb and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents such as *Bacillus thuringiensis, Bacillus thuringiensis* delta endotoxin, baculovirus, and entomopathogenic bacteria, virus and fungi.

The triazoles and strobilurins are particular effective and environmental safe fungicides. The mid-seventies saw the introduction of the fungicide group DMI or demethylation inhibitors, which contain the triazole fungicides. The triazole fungicides have been the mainstay of cereal disease control since then. The first of these to appear was triadimefon (Bayleton) and there have been new triazoles appearing on a regular basis for example, popinconazole, tebuconazole, myclobutanil and epoxiconazole. The triazoles are active against a wide range of foliar diseases and were used alone or in mixtures with non-systemic fungicides and also with the systemic morpholine group of fungicides. Over the twenty-five years since triadimefon was introduced some of the triazoles have disappeared from the marketplace as resistance to them developed and they no longer provided any benefit or advantage to control fungal diseases. Therefore, the present invention contemplates a triazole type fungicide alone or in combination with one or more fungicides with a different mode of action in an admixture with glyphosate. The mode of action of glyphosate is to inhibit the EPSPS enzyme, a mixture of glyphosate and a triazole can provide a means to prevent or reduce the development of resistance to the fungicide by providing compounds with different modes of action, hence lengthening the utility of the fungicide for use in crop production. Both glyphosate and a triazole provide systemic fungal disease control when applied together or sequentially. The present invention contemplates a method for reducing fungal resistance to a triazole fungicide by combining in an admixture a glyphosate compound and a triazole fungicide compound and treating a glyphosate tolerant plant with the admixture.

A new group of fungicides the STAR or strobilurin type fungicides, were introduced in 1997 with azoxystrobin (Amistar®). This was followed by kresoxim-methyl/epoxiconazole (Allegro®) and trifloxystrobin (Twist®) and famoxadone/flusilazole (Charisma®), which is a non-strobilurin but has a strobilurin type action. Strobilurin type fungicides are based on natural anti-fungal compounds, which some forest wood decaying mushrooms secrete to inhibit competitor fungi. They have a novel mode of action to that of the other groups of fungicide products. They are also very safe from an environmental point of view. Various formulations and fungicide mixtures are commercially available. Acanto® (Syngenta Corp) is available as a straight strobilurin (picoxystrobin), Modem® is another straight strobilurin (pyraclostrobin). Quadris® azoxystrobin, Headline® pyraclostrobin, and pyraclostrobin plus boscalid are commercially available fungicide formulations. Straight strobilurins need a non-strobilurin partner in all situations. Opera® (BASF Corp) is a pre-formulated mixture of pyraclostrobin and epoxiconazole, Stratego® (Bayer Crop- Science) fungicide is a mixture of trifloxystrobin and propiconazole, and Covershield® (BASF Corp) is a three-way mixture of pyraclostrobin, epoxiconazole and kresoxim-methyl. The mode of action of glyphosate is to systemically inhibit the EPSPS enzyme, a mixture of glyphosate and a systemic strobilurin type fungicide or fungicide mixture containing a strobilurin as described, can provide a means to prevent or reduce fungal disease and development of fungal resistance to the fungicide, hence lengthening the utility of the fungicide for crop production. Therefore, the present invention contemplates a strobilurin type fungicide alone or in combination with one or more fungicides with a different mode of action in an admixture with glyphosate. The present invention contemplates a method for reducing fungal resistance to a strobilurin fungicide by combining in an admixture a glyphosate compound and a strobilurin fungicide compound and treating a glyphosate tolerant plant with the admixture.

The chloronitriles class of fungicides, for example, chlorthalonil and chloronil are contact fungicides that are effective in preventing spore germination and reducing hyphal growth. It is contemplated that glyphosate in an admixture with a chloronitrile fungicide will be effective in preventing significant fungal infection and disease symptoms when applied to glyphosate tolerant plants. The carboxamides class fungicides, for example, boscalid, are also contact fungicides for which it is contemplated that glyphosate in an admixture with a carboxamide fungicide will be effective in preventing significant fungal infection and disease symptoms when applied to glyphosate tolerant plants. Contact fungicides provide a protective effect to plant surfaces to inhibit spore germination or hyphal growth, the added glyphosate provides an additional systemic protective effect to inhibit hyphal growth within the plant tissues.

The selection of application rates that are effective for a specific plant pathogen is within the skill of the ordinary agricultural scientist. Those of skill in the art will likewise recognize that individual plant conditions, weather and growing conditions, as well as the specific pathogen and glyphosate composition selected, will influence the degree of biological effectiveness achieved in practicing this invention. Useful application rates for the glyphosate compositions employed can depend upon all of the above conditions. Preferably, the application rate will result in a concentration of glyphosate in a plant tissue of between about 0.01 ppm to about 100 ppm per fresh weight. More preferable, tissue concentrations of between 0.1 ppm and 25 ppm glyphosate of fresh weight are obtained in the tissues of plants treated in the methods of the present invention. Most preferably, concentrations of between about 0.1 ppm and about 10 ppm or 0.5 ppm and about 10 ppm glyphosate are effective in controlling, preventing or treating disease in a treated plant. Table 1 shows glyphosate residue analysis observed in different glyphosate tolerant crop plants (RR, Round Ready®, registered trademark of Monsanto Co.) at different application dose rates, number of treatments (Trt) and developmental stage of the plant when the glyphosate was applied (R1 in soybean is first flowering, PH is xxx; in corn V4 and V8 are number of leaves; in cotton OT is PD is and PH is; in rice lf is leaf, pan ini is panicle initiation and PH is, in wheat lf is leaf, preboot is before the head emerges, and sugarbeet lf is leaf) and the tissues that were analyzed and the amount of glyphosate detected (Gly (ppm)).

TABLE 1

Glyphosate residue analysis in glyphosate tolerant crops

| | Trt | tissue | Gly (ppm) |
|---|---|---|---|
| RR soybean | 3 × 0.75 lb, V3/R1/PH | forage | 7.60 |
| | | hay | 1.30 |
| | | seed | 0.80 |
| RR corn | 2 × 0.75 lb, V4/V8 | forage | 0.73 |
| (GA21) | | grain | 0.07 |
| | | stover | 1.30 |
| RR cotton | 3 × 1.5 lb, OT/PD/PH | seed | 1.60 |
| RR canola | 0.8 lb | seed | 0.02 |
| RR rice | 1.5 lb 5 lf | grain | 0.05 |
| | | straw | 0.05 |
| | 2 × 1.12 lb, 5 lf/pan ini | grain | 3.00 |
| | | straw | 3.10 |
| | 3 × 1.12 lb, 5 lf/pan ini/PH | grain | 14.80 |
| | | straw | 6.90 |
| RR wheat | 0.75 lb, 4 lf | forage | 2.30 |
| | | hay | 1.20 |
| | | grain | 0.50 |
| | | straw | 0.50 |
| | 2 × 0.75 lb, 4 lf/Preboot | forage | 2.60 |
| | | hay | 13.00 |
| | | grain | 7.50 |
| | | straw | 5.30 |
| RR sugarbeet | 3 × 0.75 lb, 2 lf/6 lf/12 lf | tops | 0.40 |
| | | beet | 0.50 |
| | 3 × 0.75, | tops | 4.30 |
| | 2 lf/12 lf/12 lf + 30 d | beet | 6.60 |
| RR potato | 2 × 1.5 lb, 2 lf/row closure | tubers | 4.10 |
| | 3 × 1.5 lb, 2 lf/row clo/PH | tubers | 8.60 |

In one aspect, a rate of application of a composition from about 0.1 lb/acre to about 5 lb/acre of glyphosate is effective in controlling, preventing or treating a pathogen in accordance with a method of the present invention. Yet more preferable are rates of application ranging from about 0.5 lb/acre to about 2.5 lb/acre. Most preferable are rates of application of about 0.75 lb/acre. When glyphosate is used in mixtures with fungicides or as sequential applications of glyphosate and the fungicide, the rates may be reduced in order to achieve the most efficient ratio of an effective concentration of glyphosate and the fungicide to provide a cost effective disease control mixture. The present invention demonstrates that application of glyphosate and a fungicide provides a synergistic benefit. A 1× rate of glyphosate (0.75 lb/acre) followed by a 0.5× rate of a fungicide compound as shown in Table 3 in Example 8 will provide equivalent or enhanced fungal disease control as compared to a 2× rate of glyphosate or a 1× rate of a fungicide. It is contemplated that further reductions in application rates using a glyphosate and fungicide admixture will be effective to control fungal diseases. For example, a 1× rate of glyphosate mixed with a 0.4× rate of fungicide, or 0.3×, or 0.2×, or 0.1× rate or rates in between may be cost effective for the economic control of fungal diseases. Additionally, a reduced rate of glyphosate in the mixture may also provide effective and cost efficient control of fungal diseases, for example, a 0.75× rate of glyphosate with a 0.5× rate of a fungicide, or a 0.5× rate of glyphosate with a 0.5× rate of fungicide, or a 0.25× rate of glyphosate with a 0.5× rate of fungicide, or a 0.1× rate of glyphosate with a 0.5× rate of fungicide. A ratio of 0.1× glyphosate and 0.1× fungicide in an admixture is contemplated in the present invention, the exact ratio can be determined by the effective amount of each compound that is delivered to the diseased or disease susceptible plant tissues and by those skilled in the art of chemical formulation and application for the control of fungal diseases of plants.

Application of glyphosate compositions to foliage of plants is preferably accomplished by spraying, using any conventional means for spraying liquids, such as spray nozzles or spinning-disk atomizers. Compositions of the present invention can be used in precision farming techniques, in which apparatus is employed to vary the amount of exogenous chemical substance applied to different parts of a field, depending on variables such as the particular plant species present, plant growth stage, soil moisture status, etc. In one aspect of such techniques, a global positioning system operated with the spraying apparatus can be used to control application of the composition in desired amounts to different parts of a field.

A glyphosate composition is preferably dilute enough to be readily sprayed using standard agricultural spray equipment. Suitable application rates for the present invention vary depending upon a number of factors, including the type and concentration of active ingredient and the plant species involved. Useful rates for applying an aqueous composition to a field of foliage can range from about 25 to about 1,000 liters per hectare (1/ha), preferably about 50 to about 300 l/ha, by spray application.

III. Plants

In one aspect of the present invention, a method is provided for the application of a glyphosate composition for disease control, prevention or treatment results in decreased need for fungicide treatment of plants or plant parts, thus lowering costs of material, labor, and environmental pollution, or prolonging shelf-life of products (e.g. fruit, seed, and the like) of such plants. In a preferred aspect of the method the glyphosate composition further comprises a fungicide compound. The term "plant" includes whole plants and parts thereof, including, but not limited to, shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, and the like), and progeny of same. The class of plants that can be used in a method of the invention includes the class of higher and lower plants, including angiosperms (monocotyledonous and dicotyledonous plants), gymnosperms, ferns, horsetails, psilophytes, lycophytes, bryophytes, and multicellular algae. Preferably, plants for use in the methods of the present invention include any vascular plant, for example monocotyledons or dicotyledons or gymnosperms, including, but not limited to alfalfa, apple, *Arabidopsis*, banana, barley, canola, castor bean, chrysanthemum, clover, cocoa, coffee, cotton, cottonseed, corn, crambe, cranberry, cucumber, dendrobium, dioscorea, eucalyptus, fescue, flax, gladiolus, liliacea, linseed, millet, muskmelon, mustard, oat, oil palm, oilseed rape, papaya, peanut, pineapple, ornamental plants, *Phaseolus*, potato, rapeseed, rice, rye, ryegrass, safflower, sesame, sorghum, soybean, sugarbeet, sugarcane, sunflower, strawberry, tobacco, tomato, turfgrass, wheat and vegetable crops such as lettuce, celery, broccoli, cauliflower, cucurbits; fruit and nut trees, such as apple, pear, peach, orange, grapefruit, lemon, lime, almond, pecan, walnut, hazel; vines, such as grapes, kiwi, hops; fruit shrubs and brambles, such as raspberry, blackberry, gooseberry; forest trees, such as ash, pine, fir, maple, oak, chestnut, popular; with alfalfa, canola, castor bean, corn, cotton, crambe, flax, linseed, mustard, oil palm, oilseed rape, peanut, potato, rice, safflower, sesame, soybean, sugarbeet, sunflower, tobacco, tomato, and wheat preferred. More preferably, plants for use in the methods of the present invention include any crop plant, for example, forage crop, oilseed crop, grain crop, fruit crop, vegetable crop, fiber crop, spice crop, nut crop, turf crop, sugar crop, beverage crop, and forest crop. In a highly preferred aspect, the crop plant used in a method is a soybean plant. In another highly preferred aspect, the crop plant is wheat. In another highly preferred aspect, the crop plant is corn. In another highly preferred aspect, the crop plant is cotton. In another highly preferred aspect, the crop plant is alfalfa. In another highly preferred aspect, the crop plant is sugarbeet. In another highly preferred aspect, the crop plant is rice. In another highly preferred aspect, the crop plant is potato. In another highly preferred aspect, the crop plant is tomato.

In a preferred aspect, the methods use plants that are tolerant to glyphosate. Such plants include crop plants that have been modified to be tolerant of glyphosate. Such plants may be modified through traditional breeding techniques, or modern breeding techniques such as genetic engineering. In one preferred aspect of the present invention, the plants used in the methods are transgenic plants expressing genes providing tolerance to glyphosate. Glyphosate tolerance may be imparted to plant species by recombinant DNA techniques that are described in the art (as described for example by U.S. Pat. Nos. 5,312,910; 5,310,667; 5,463,175 (all of which are incorporated by reference in their entirety)). Preferably, glyphosate tolerance is brought about by inserting a gene encoding a modified or naturally occurring 5-enolpyruvylshikimate-3-phosphate synthase (EPSPS) enzyme into the genome of a plant. A modified EPSPS imparts glyphosate tolerance to a plant by being less inhibited by glyphosate than is the EPSPS native to the plant. The source of the gene encoding modified EPSPS may be a bacterial strain that has naturally developed an EPSPS resistant to glyphosate, a synthesized double-stranded deoxyribonucleic acid designed to encode a modified EPSPS, or any other source.

For example, a gene for EPSP synthase has been isolated from *Agrobacterium tumefaciens* strain CP4, having lower susceptibility to glyphosate (U.S. Pat. No. 5,633,435 (incorporated by reference in its entirety)) and when expressed as a transgene in plants confers a high level of glyphosate tolerance to the plants. In addition, other EPSPS variants that have lower affinity for glyphosate and therefore retain their catalytic activity in the presence of glyphosate have also been described (U.S. Pat. Nos. 4,940,835, and 5,094,945 (both of which are incorporated by reference in their entirety)). These variants typically have a higher Ki for glyphosate than the wild-type EPSPS enzyme which confers the glyphosate tolerant phenotype, but these variants can also be characterized by a high Km for PEP which makes the enzyme kinetically less efficient (Kishore and Shah, Ann. Rev. Biochem. (1988) 57:627-663; Sost et al., FEBS Lett. (1984) 173:238-241; Shulze et al., Arch. Microbiol. (1984) 137:121-123; Kishore et al., Fed. Proc. (1986) 45:1506; Sost and Amrhein, Arch. Biochem. Biophys. (1990) 282:433-436). Furthermore, high levels of glyphosate tolerance has been achieved in a number of crop plants by fusing EPSPS to a chloroplast transit peptide (CTP) for targeted expression in plastids. Glyphosate tolerance can also be achieved in plants through inserting into the plant genome a DNA molecule that causes the production of higher levels of wild-type EPSPS (Shah et al., Science 233:478-481 (1986). Particularly preferred methods for achieving glyphosate tolerance in the methods of the present invention involve genes that allow for the conservation of glyphosate in the plant tissue that is affected by the plant pathogen.

Lines of transgenic glyphosate tolerant crop plants contemplated for use in the methods of the present invention include corn, cotton, soybean, sugarbeet, alfalfa, wheat, among others, that express a gene imparting glyphosate tolerance have been commercialized or are currently in commercial stages of development, for example, Roundup Ready® Cotton 1445 (U.S. Pat. No. 6,740,488 (incorporated by reference in its entirety)), Roundup Ready® corn GA21 and nk603 (U.S. Pat. No. 6,825,400 (incorporated by reference in its entirety)), and Roundup Ready® Sugarbeet (U.S. Patent Pub 20040172669A1 (incorporated by reference in its entirety)), Roundup Ready® Canola RT73 (US20040018518A1 (incorporated by reference in its entirety)), and Roundup Ready® Soybean 40-3-2. Additional Roundup Ready® crops underdevelopment by Monsanto Co, St Louis, Mo. include wheat MON71800 (U.S. Pat. No. 6,689,880 (incorporated by reference in its entirety)), enhanced Roundup Ready® cotton 88913 (WO 04/072235 (incorporated by reference in its entirety)), Roundup Ready® alfalfa J-101 and J-163 (WO 04/070020 (incorporated by reference in its entirety)), and ASR368 bentgrass (WO 04/053062 (incorporated by reference in its entirety)). Production of transgenic lines of other plant species expressing a glyphosate-tolerance gene may be produced by techniques known in the art. See, e.g. U.S. Pat. Nos. 5,312,910; 5,310,667; 5,463,175 (all of which are herein incorporated by reference in their entirety).

A "transgenic plant" refers to a plant that contains genetic material not found (i.e. "exogenous") in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to appropriate inducible or constitutive regulatory sequences that allow for the expression of the polypeptide. The expression cassette can be introduced into a plant by transformation or by breeding after transformation of a parent plant. As previously described a plant refers to a whole plant, including seedlings and mature plants, as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

The plant or plant part for use in the present invention include plants of any stage of plant development. Preferably, the application occurs during the stages of germination, seedling growth, vegetative growth, and reproductive growth. More preferably, applications of the present invention occur during vegetative and reproductive growth stages. The stages of vegetative and reproductive growth are also referred to herein as "adult" or "mature" plants.

IV. Pathogens

The methods of the present invention find use in the control, prevention or treatment of a wide variety of plant pathogens. The methods of the present invention include prophylactic inhibition and therapeutic treatment of infection by plant pathogens. Preferably, the methods of the present invention inhibit or treat plant pathogenic fungi and bacteria. The plant pathogens inhibited in the methods of the present invention preferably include those that produce aromatic amino acids, such as phenylalanine, tyrosine, and tryptophan, through the shikimate biosynthetic pathway. Combinations of glyphosate and chemical inhibitors of enzymes that metabolize glyphosate, metabolize or oxidize shikimate or 3-phosphoshikimate (for example, quinate-shikimate dehydrogenase), or prevent plant pathogens from sequestering glyphosate can function to broaden the spectrum of plant pathogens that are susceptible to inhibition by glyphosate. Plant pathogens can be classified by their life cycle in relation to a plant host, these classifications include, obligatge parasites, facultative parasites, and facultative saprophytes. Obligate parasites can only survive and reproduce by obtaining nutrition from living plant cells and are in direct contact with these cells, examples of obligate fungal parasites of plants include, but are not limited to members of Uredinales (rusts), Ustilaginales (smuts and bunts), Erysiphales (powdery mildews), and Oomycetes (water molds and downy mildews). Facultative parasites are organisms that generally survive as saprophytes on the products of other organisms or dead organisms but can become parasitic when the conditions are favorable. Facultative saprophytes are organisms that generally survive as parasites of plants but can survive as saprophytes when a susceptible plant host is not available.

The method of the present invention can be used to control, prevent or treat infection from a wide array of plant pathogens that include obligate parasites, facultative parasites, and facultative saprophytes, which include, but are not limited to the following: Ascomycete fungi such as of the genera *Venturia, Podosphaera, Erysiphe, Monolinia, Mycosphaerella*, and *Uncinula*; Basidiomycete fungi such as from the genera *Hemileia, Rhizoctonia*, and *Puccinia*; Fungi imperfecti such as the genera *Botrytis, Helminthosporium, Rhynchosporium, Fusarium* (i.e., *F. monoliforme*), *Septoria, Cercospora, Alternaria, Pyricularia*, and *Pseudocercosporella* (i.e., *P. herpotrichoides*); Oomycete fungi such as from the genera *Phytophthora* (i.e., *P. parasitica. P. medicaginis, P. megasperma*), *Peronospora* (i.e, *P. tabacina*), *Bremia, Pythium*, and *Plasmopara*; as well as other fungi such as *Scleropthora macrospora, Sclerophthora rayissiae, Sclerospora graminicola, Peronosclerospora sorghi, Peronosclerospora philippinensis, Peronosclerospora sacchari* and *Peronosclerospora maydis, Physopella zeae, Cercospora zeae-maydis, Colletotrichum graminicola, Gibberella zeae, Exserohilum turcicum, Kabatiellu zeae, and Bipolaris maydis*; and bacteria such as *Pseudomonas syringae, Pseudomonas tabaci*, and *Erwinia stewartii*; and mycoplasma, mycoplasma-like, rickettsia and rickettsia-like organisms, for example Pierce's disease, Alfalfa Dwarf, Phony Peach disease, Aster Yellows disease, Peach X-disease, corn stunt, and Peach Yellow disease. Particularly preferred pathogens include, but are not limited to: *Puccinia, Rhizoctonia*, GGT, stripe rust, Asian soybean rust (*Phakopsora pachyrhizi*), *Fusarium* species, *Verticillium* species, gray leaf spot, *Phytophthora* species and corn rust.

Thus, the diseases controlled, prevented or treated include, for example, diseases of alfalfa plants such as root rot (*Phytophora medicaginis, P. megasperma*); rice plant such as rice blast (*Pyricularia oryzae*), *Helminthosporium* leaf blight (*Helminthosporium oryzae, Cochliobolus miyabeanus*), Bakanae disease (*Gibberella fujikuroi*), seedling blight (*Rhizopus oryzae*), sheath blight (*Rhizoctonia solani*), and so on, those of oat such as crown rust (*Puccinia coronata*), and so on, those of barley such as powdery mildew (*Erysiphe graminis*), scald (*Rhynchsporium secalis*), spot-blotch (*Cochliobolus sativus*), yellow mottleleaf (*Helminthosporium gramineum, Pyrenophora gramineum*), net blotch (*Pyrenophra teres*), stinking smut (*Tilletia caries*), loose smut (*Ustilago nuda*), and so on, those of wheat such as powdery mildew (*Erysiphe graminis*), glume-blotch (*Leptosphaeria nodorum, Septoria nodorum*), stripe rust (*Puccinia striiformis*), *Typhula* snow blight (*Typhula incarnata*), eye spot (*Pseudocercosporella herpotrichoides*), snow mold (*Calonectria graminicola, Fusarium nivale*), stem rust (*Puccinia graminis*), black snow blight (*Typhula ishikariensis*), scab (*Gibberella zeae*), leaf rust (*Puccinia recondita, Puccinia triticina*), stripe (*Helminthosporium gramineum*), stinking smut (*Tilletia caries*), speckled leaf blight (*Septoria tritici*), loose smut (*Ustilago tritici*), and so on, those of corn such as damping-off (*Pythium debaryanum*), and so on, those of rye such as purple snow mold (*Fusarium nivale*), and so on, those of potato such as late blight (*Phytophthora infestans*), and so on, those of tabacco plant such as downy mildew (*Peronospora tabacina*), foot rot (*Phytophthora parasitica* var), septoria blight (*Cercospora nicotianae*), mosaic disease (tobacco mosaic virus), and so on, those of sugar beet such as leaf spot (*Cercospora beticola*), damping-off (*Pythium debaryanum, Rhizoctonia solani, Pythium aphanidermatum*), and so on, those of paprika such as gray mold (*Botrytis cinerea*), and so on, those of kidney bean such as gray mold (*Botrytis cinerea*), *sclerotinia* seed rot (sclerotial rot) (*Sclerotinia sclerotiorum*), southern blight (*Corticium rolfsii*), and so on, those of broad bean such as powdery mildew (*Erysiphe polygoni, Sphaerotheca fuliginea*), rust (*Uromyces fabae, Uromyces phaseoli*), gray mold (*Botrytis cinerea*), and so on, those of peanut such as Ascochyta spot (*Mycosphaerella arachidicola*), and so on, those of cabbage such as damping blight (*Rhizoctonia solani*), and so on, those of cucumber such as powdery mildew (*Sphaerotheca fuliginea*), stem rot (*Fusarium oxysporum*), gummy stem blight (*Mycosphaerella melonis*), downy mildew (*Pseudoperonospora cubensis*), gray mold (*Botrytis cinerea*), sclerotial seed rot (*Sclerotinia sclerotiorum*), anthracnose (*Colletotrichum lagenarium*), damping blight (*Fusarium oxysporum, Pythium aphanidermatum, Rhizoctonia solani*), mosaic disease (Cucumber mosaic virus), and so on, those of KOMATSUNA such as *Alternaria* sooty spot (*Alternaria brassicicola*), club root (*Plasmodiophora brassicae*), and so on, those of celery such as speckled leaf blotch (*Septoria apii*), and soon, those of radish such as yellows (*Fusarium oxysporum*), and so on, those of tomato such as *Fusarium* wilt (*Fusarium oxysporum*), foot rot (*Phytophthora infestans*), ring leaf-spot (*Alternaria solani*), gray mold (*Botrytis cinerea*), leaf blight (*Phytophthora capsici*), black rot (*Alternaria* tomato), and so on, those of eggplant such as brown rot (*Phytophthora capsici*), vascular wilt pathogens, e.g. *Verticillium* wilt (*Verticillium albo-atrum. V. dahliae*), and so on, those of Chinese cabbage such as black rot (*Alternaria japonica*), club root (*Plasmodiophora brassicae*), and so on, those of sweet pepper such as foot rot (*Phytophthora capsici*), gray mold (*Botrytis cinerea*), and so on, those of lettuce such as gray mold (*Botrytis cinerea*), and so on, those of citrus fruits such as pod and stem blight (*Diaporthe citri*), and so on, those of pear such as scab (*Venturia nashicola*), black rot (*Alternaria* kikuchiana), brown-spot (*Gymnosporangium haraeanum*), and so on, those of grape such as downy mildew (*Plasmopara viticola*), gray mold (*Botrytis cinerea*), *Sphaceloma* scab (*Elsinoe ampelina*), and so on, those of peach such as leaf curl (*Taphrina deformans*), shot hole (*Mycosphaerella cerasella*), and so on, those of apple such as powdery mildew (*Podosphaera leucotria*), scab (*Cladsporium carpophilum*), gray mold (*Botrytis cinerea*), black rot (*Venturia inaegualis*), brown spot (*Gymnosporangium yamadae*), white root rot (*Rosellinia nectrix*), *Alternaria* leaf spot (*Alternaria mali*), and so on, and other deseases of grains, fruits and vegetables such as oil-seed rape, sunflower, carrot, pepper, strawberry, melon, kiwi fruit, onion, leek, sweet potato, fig, ume, asparagus, persimmon, soybean, adzukibean, watermelon, crown daisy, spinach, tea and so on. Thus, compound (I.sup.0) or salts thereof show high activities against deseases caused by microorganisms of, especially, the genus *Pyricularia, Cochliobolus, Curvularia, Pyrenophora, Alternaria*, and others akin to them. Examples of diseases caused by those microbes, include rice blast, *Helminthosporium* leaf spot, and discolored rice grains of rice plant, spot-blotch, stripe, and net blotch of barley, stripe and spot-blotch of wheat, *Helminthosporium* leaf spot of corn, early blight of potato, *Alternaria* sooty spot of HAKUSAI, ring leaf-spot and black rot of tomato, black rot of Chinese cabbage, black rot of pear, and *Alternaria* leaf spot of apple, and so on.

Figure 2:
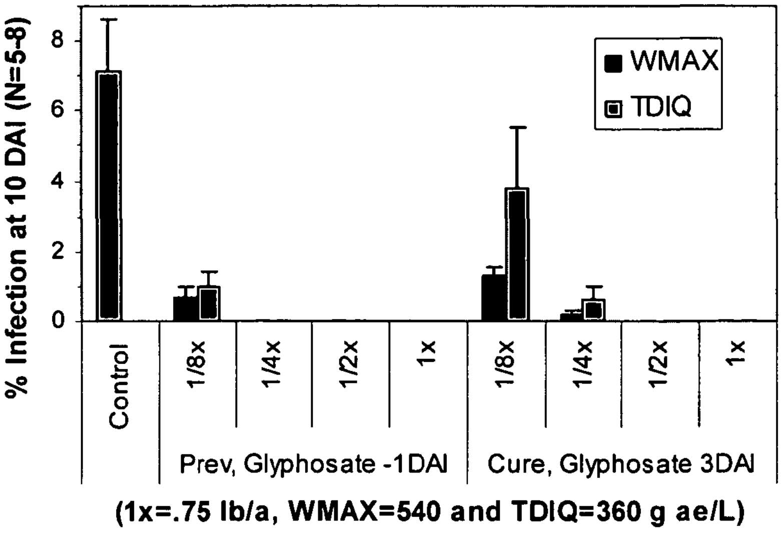
FIG. 2 shows the comparison of Roundup WeatherMAX® and Touchdown™ IQ for controlling wheat rust disease when applied before (preventative) or after (curative) inoculation with wheat rust spores, glyphosate formulation were applied at ⅛× to 1× rates in Roundup Ready Wheat®.

Not all plant pathogens will be equally susceptible to the inhibitory effects of the current formulations of glyphosate compositions. It has been observed in the present invention that differences exist in the current commercially available formulations in there effects on plant disease. For example, FIG. 2 compares Roundup WeatherMAX® (Monsanto Co. St Louis, Mo.) and Touchdown™ IQ (Syngenta Corp) glyphosate formulations, the results demonstrate that WeatherMAX® provides superior disease control over Touchdown®. WeatherMAX® has been specifically formulated to provide rapid uptake of glyphosate into plant tissues. Plant pathogens that are in contact with plant cells and tissues (for example, vascular tissue) and exchange chemicals with the plant cells or tissues will be more effectively suppressed if the glyphosate applied to the plant is more rapidly absorbed and translocated to the sites of pathogen infection. It is contemplated by the inventors that improvements can be made to the current formulations to provide a glyphosate composition specifically formulated for use in pathogen control on glyphosate tolerant plants. Current formulations have been designed for the uptake in weed species, generally for treatment of weed seedlings and weeds in a rapid growth stage. It is contemplated that glyphosate formulations for disease control will be applied to the crop plant at a later growth stage, for example, when the plant is flowering or in the process of producing seeds or fruit, it is at these stages of development that plant diseases can have the greatest effect on crop yield. Leaves are the source tissues that provide the products of photosynthesis needed for plant growth, seed, fruit and storage organ development. Protecting these leaves from disease due to fungal infection is important to protect yield of the crop. The flag leaf of monocot crops contributes substantially to the yield of the crop, protecting this leaf from disease is particularly important in protecting monocot crop yield. Leaves of dicot crops generally provide the products of photosynthesis to the closely associated fruiting structures of the plant, protecting these leaves from disease is particularly important in protecting dicot crop yields. Roots provide water and mineral nutrients to the plants, protecting roots from disease is also particularly important in maintaining yield of the crop plant. Enhanced formulations for systemic (includes both locally systemic and whole plant systemic) uptake may include the addition of adjuvants, for example, alkoxylated fatty amines, organosilicones, nonyl phenol ethylene oxide condensate, and others known in the art. Examples of suitable adjuvants that enhance the uptake and efficacy of glyphosate include polyoxyalkylene alkylamines, polyoxyalkylene alkylammonium salts, polyoxyalkylene alkylamine oxides, polyoxyalkylene tertiary and quaternary etheramines, polyoxyalkylene etheramine oxides, mono- and di- (polyoxyalkylene alcohol) phosphates, polyoxyalkylene alkylethers and combinations thereof. Preferred adjuvants are polyoxyethylene coco and tallow amines, polyoxyethylene $C_{8-18}$ alkyl oxypropyl amines, polyoxyethylene $C_{16-22}$ alkylethers and combinations thereof. Examples of these adjuvants can be found in U.S. Pat. Nos. 5,668,085, 5,683,958, 5,703,015, 6,063,733, 6,121,199, 6,121,200, 6,184,182, 6,245,713, 6,365,551, RE37,866 and U.S. Patent Application Pub. No. US2003/0104943 A1 (all of which are herein incorporated by reference in their entirety).

It is further contemplated that glyphosate formulations with combinations of surfactants that provide greater contact with the plant pathogen on a leaf surface by retaining and spreading the glyphosate onto the leaf surface will also enhance the glyphosate effect on the pathogen. These formulations provide surfactants for the spread of the glyphosate composition across the leaf surface and enhance the contact and uptake of glyphosate into a fungal spore or hyphae, so that when a pathogen contacts a leaf surface so treated, it will also contact the glyphosate. Additionally, surfactants used in contact fungicides may enhance the uptake of glyphosate into the fungal cell when the formulation is in contact with a fungal spore or hyphae.

Disease resistance evaluation can be performed by methods known in the art. See, Uknes et al, (1993) Molecular Plant Microbe Interactions 6: 680-685; Gorlach et al., (1996) Plant Cell 8:629-643; Alexander et al., Proc. Natl. Acad. Sci. USA 90: 7327-7331 (1993). The skilled artisan will recognize that methods for determining plant infection and disease by a plant pathogen depends on the pathogen and plant being tested.

The following examples are included to demonstrate aspects of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific aspects which are disclosed and still obtain a like or similar result without departing from the spirit and scope of the invention.

EXAMPLES

Example 1: In Vitro Effects of Glyphosate on Plant Pathogens

In vitro screens identified glyphosate as a very weak fungicide against a series of pathogenic organisms. Table 2 shows that when various fungal plant pathogens are grown on growth media containing various concentrations of glyphosate to measure $EC_{90}$ concentrations (the concentration for 90% of maximal effect of, e.g., inhibiting fungal cell proliferation or statistically reducing the level fungal growth). These data demonstrate a high concentration of glyphosate is required to inhibit fungal growth in vitro. It was therefore a surprising result when it was observed that glyphosate tolerant plants when treated with glyphosate showed resistance to fungal disease. The glyphosate residue analysis shown in Table 1 would have suggested that the levels of glyphosate in the plant tissues to be too low for effective inhibition of fungal pathogens. The susceptibility of fungal pathogens to glyphosate effects may change when the pathogen is in contact with plant cells. The chemical exchange that occurs between a fungal pathogen and the host plant cell allows for the importation of glyphosate into the fungal cell that is not evident in an in vitro assay.

TABLE 2

In vitro effects of glyphosate on fungal cell growth

| Fungus | In vitro $EC_{90}$, ppm | Crop of interest |
|---|---|---|
| *Septoria* | <100 | Wheat |
| *Pseudocercosporella* | <100 | Wheat |
| *Botrytis* | <100 | Veg/strawberry |
| *Phytophthora* | 1000 | Potato/soy |
| *Rhizoctonia* | 1000 | Wheat/potato |
| *Fusarium* | 1000 | Wheat/potato |
| *Gaeumannomyces* | 1000 | Wheat |
| *Puccinia* | 5000 | Wheat |
| *Pyricularia* | 5000 | Rice |

Example 2: Disease Treatment in Glyphosate Tolerant Wheat

Compositions of water, surfactant (a 0.1% solution), glyphosate formulations (WeatherMAX® (glyphosate-K salt), UltraMAX® (glyphosate-IPA salt), or a glyphosate composition without surfactant (IPA-salt) are applied to glyphosate tolerant wheat plants at different growth stages that have been previously inoculated with leaf rust (*Puccinia triticina*) to test for disease control. Three, five and seven-leaf stage wheat plants are inoculated with *Puccinia triticina* spores and incubated to allow for spore germination.

Plants are evaluated for disease at one day after treatment (1DAT) with the above compositions. In addition, wheat plants at the 5 leaf stage are used as an untreated control.

All eleven (11) untreated wheat plants exhibited significant leaf rust symptoms. Seven out of eight water-treated wheat plants (3-leaf stage) showed disease symptoms. Similarly, surfactant-treated plants at the 3 leaf and 7 leaf stages exhibited nearly complete disease infection. Six out of eight 3-leaf stage wheat plants showed disease symptoms at 1DAT, while all four 7-leaf stage wheat plants showed disease symptoms.

In contrast, plants treated with glyphosate compositions demonstrated substantially total disease control. Disease treatment was achieved using an application rate of 1× (equals 0.75 lb/acre through the $5^{th}$ leaf). In wheat plants at the 5-leaf stage treated with a 1× glyphosate composition (Roundup WeatherMAX® formulation), none of the 11 treated plants showed disease symptoms. In 3-leaf stage plants, none of the 8 inoculated plants showed disease symptoms and none of the 4 inoculated 7-leaf stage plants showed signs of infection after treatment with a 1× Roundup WeatherMAX® application.

These results demonstrate that glyphosate compositions can be used to treat fungal infection, such as leaf rust, in glyphosate-tolerant wheat plants.

Example 3: Correlation of Tissue Glyphosate Concentration and Disease Prevention To determine the correlation between glyphosate concentration in plant tissue and disease control, glyphosate tolerant wheat plants are treated with glyphosate compositions prior to inoculation with *Puccinia* spores. Four different regimens are employed. First, whole plants, either 3-leaf or 5-leaf stage, are treated with a 1× spray of WeatherMAX Roundup® glyphosate composition. A single mature leaf from each treated plant is inoculated with *Puccinia* spores either 1 day or 14 days after glyphosate application. The inoculated plants are then incubated for 24 hours at 100% relative humidity for germination of the spores. Twelve days after inoculation, disease conditions are evaluated and concentrations of glyphosate in the plant tissue is quantitated. Disease conditions are evaluated macroscopically for pustule development and lesion development.

Disease symptoms were prevented in inoculations both at 1 day after glyphosate treatment and 14 days after treatment. FIG. 1 shows that control plants not treated with glyphosate demonstrated about 25% to about 30% pustule development 12 days after inoculation. In contrast, plants treated with glyphosate showed less than 1% pustule development 12 days after inoculation.

Furthermore, disease prevention directly correlates with tissue glyphosate concentrations. For example, lesion and pustule development are prevented at tissue concentrations of glyphosate of 20 to 80 ppm, while pustule development is prevented by as low as about 10 ppm glyphosate. Autoradiograms of leaves treated with 14C-glyphosate confirmed that glyphosate concentrations are uniformly distributed throughout the inoculated leaf.

Example 4: Comparison of Roundup® WeatherMAX Formulation to Touchdown™ IQ Formulation Various formulations of glyphosate are commercially available. The inventors contemplated that these formulations may vary in their ability to affect fungal disease development. The results of a comparison of WeatherMAX® and Touchdown™ IQ performed on Roundup Ready wheat to control wheat leaf rust either as a preventative or curative application is shown in FIG. 2. The rates of the formulation applications were from ⅛x to 1×. The treatments were at one day after inoculation with rust spores (1DAI) or three days after inoculation (3DAI). Rust disease was measured 10 days after inoculation by determining the percent leaf infection. Both formulations demonstrated the ability to reduce percent leaf infection, with the WeatherMAX® formulation providing a greater benefit than the Touchdown™ formulation a lower dose rates. The present invention provides for the use of WeatherMAX® formulation and effective application rates thereof for the treatment of fungal disease on glyphosate tolerant plants. Additional glyphosate formulations are contemplated that provide enhanced uptake in glyphosate tolerant plants or enhanced uptake in plant pathogens, in particular fungal pathogens.

Example 5: Translocation of Glyphosate for Disease Prevention 14C-glyphosate is sprayed over-the-top to wheat plants using field application conditions and use rates. The top fully-expanded leaf (one leaf) is shielded from the spray (the untreated leaf). The untreated leaf is manually infected with *Puccinia* spores one day after treatment (1DAT) with glyphosate to generate leaf rust.

Analysis at 11 days after inoculation (DAI) with *Puccinia* show a decrease in disease incidence with an increase in spray dose. Analysis of glyphosate in the shielded leaf show a decrease in disease with an increase in tissue glyphosate at 0 or 11 DAI. Complete disease prevention was attained at 1.3 ppm glyphosate from spray application of ½× of Roundup®. Since the untreated leaf is shielded from the spray, glyphosate in tissues arose strictly from phloem translocation. The results indicate that phloem-mobilized glyphosate is associated with the observed disease prevention and the rust pathogen obtained the glyphosate from contact with plant tissue containing the systemically translocated glyphosate.

Example 6: Systemic Acquired Resistance

To test whether disease control, prevention or treatment correlates with the induction of Systemic Acquired Resistance (SAR) time-course Northern blot analysis are conducted as described herein.

Glyphosate tolerant wheat plants (3-4 leaf stage) are separated into three (3) groups and sprayed with one of the following compositions: a 0.1% surfactant blank from Roundup® (WeatherMAX), Roundup® WeatherMAX (0.75 lb/acre), or INA (2,6-dichloro isonicotinic acid, 200 ppm in 0.1% surfactant blank). One-half of the plants from each of the three treatments are sampled from 0 to 144 hours after treatment for induction of SAR genes.

The remaining treated plants are inoculated with leaf rust spores (*Puccinia triticina*) one day after treatment with one of the three compositions. The inoculated plants are incubated in a dew chamber for 24 hours. Leaf tissues from the inoculated plants are collected at time points from 0 to 120 hours after inoculation.

Leaf tissue from each sampling is homogenized and total RNA is isolated following standard methods. The total RNA is separated on an Agarose gel, and transferred to nitrocellulose membrane for use in Northern hybridizations. The membranes containing the separated total RNA are hybridized with radiolabeled representative SAR genes, WIR2 (PR5) and WCI3.

Northern blot analysis revealed that the PR5 gene is induced in leaf tissues of all 3 treatments as well as spore inoculation. However, plants treated with Roundup WeatherMAX® are the only plants lacking infection. Northern results indicated that induction of the PR5 induction gene did not correlate with disease control, and therefore is not responsible for leaf rust resistance. The WCI3 gene is induced by INA treatment but also did not confer leaf rust resistance. The Northern results indicate that induction of the tested SAR genes does not correlate with resistance to leaf rust in RR wheat.

Example 7: Glyphosate as a Post-Infection Treatment

To determine if glyphosate could treat disease post-infection, one top leaf of glyphosate tolerant wheat plants (3-leaf stage) is inoculated with rust spores. Depending on the treatment to be used, the spores are then allowed to germinate. Seven treatments are employed: 1) no treatment, 2) surfactant treatment before spore inoculation, 3) surfactant after spore inoculation, but before spore germination, 4) 1× glyphosate after inoculation before germination, 5) 1× glyphosate after germination (0 days after inoculation (DAI), 6) 1× glyphosate at 1DAI, and 7) 1× glyphosate at 4DAI (lesions were already present). Disease incidence is evaluated 11 DAI.

Plants left untreated or treated only with surfactant show infection levels of between 10% and about 25%, FIG. 1. In contrast, plants treated with glyphosate show either no infection or no progression to an existing infection. For example, the plants treated with 1× glyphosate at 4DAI in which lesions are already present at the time of treatment showed no development of pustules. In contrast, untreated plants show substantial development of pustules. These results indicate that glyphosate compositions can be used to treat fungal infections in plants.

Example 8: Glyphosate to Control, Prevent or Treat Soybean Rust

Asian soybean rust is an aggressive foliar disease of soybean that occurs where soybeans are grown in Asia, and more recently, in southern Africa, Paraguay, Argentina and Brazil. *Phakopsora pachyrhizi*, the fungus that causes Asian soybean rust, has been found in the continental United States. Glyphosate compositions are used to control, prevent or treat disease in glyphosate tolerant soybean plants (RR) under field conditions. A single application rate of Roundup® (1×=0.75 lbs ae/acre or 0.84 kg ae/ha) or multiple applications are applied times to a rust susceptible variety of soybean. The Roundup® treated plants are not treated with any fungicide and allowed to be naturally infected with Asian soybean rust. In addition, glyphosate-tolerant soybean plants can be grown in a greenhouse and manually infected with spores to induced disease infection.

The treated and untreated plants are observed for disease incidence and results obtained for using glyphosate compositions in glyphosate tolerant soybean plants to control, prevent or treat rust. Rust development is delayed 7-10 days in RR soybean (sprayed at ~V4 stage), as compared to conventional soy. Rust severity is less in RR soybean as compared to conventional soybean in early season observations. This effect was observed in multiple RR soybean varieties, and at multiple field locations in Brazil. Frequent low to moderate rates of glyphosate treatment during the growing season provides a decrease in disease incidence of Asian soybean rust.

A study was conducted in a greenhouse in Brazil to confirm the earlier field observations and to test for the effects of combining a glyphosate and a fungicide treatment. Two Roundup Ready® soybean cultivars, RR8000 and RR8045 that contain the 40-3-2 transgene insert were treated with glyphosate and a fungicide (Opera®). The treatments (trt) were Treatment 1—no glyphosate spray and no Opera® fungicide, Treatment 2—1× glyphosate, no Opera® fungicide applied every two weeks starting at V3 (V3=third vegetative leaf) until final disease rating; Treatment 3—2× glyphosate, no Opera® fungicide every two weeks starting at V3 until final disease rating.

Treatment 4—no glyphosate, 1× Opera® according to manufacturer's label, every two weeks starting at V3 until final disease rating; Treatment 5—no glyphosate, 0.5× Opera®, every two weeks starting at V3 until final disease rating; Treatment 6—1× glyphosate, 0.5× Opera® sequential sprays, every two weeks starting at V3 until final disease rating. The results are shown in Table 3. The plants of the RR8000 and RR8045 cultivars with treatment 1, no spray treatment, showed rust disease of 81.7 and 93.3 percent, respectively. The treatment 2, 1× glyphosate treatment, demonstrated a reduction in the percent rust disease up to the 56 day time point; treatment 3, 2× glyphosate, showed a high level of disease reduction at the first three time points for RR8000 and RR8045, increasing to 30.0 percent and 73.3 percent at the 56 day time point. Treatment 4, Opera® 1×, showed a high level of disease reduction in both cultivars at all time points. Treatment 5, Opera® 0.5×, showed a high level of disease control for the first two time points, then increasing to 30.0 and 33.3 at the 56 day time point. Treatment 6, 1× glyphosate plus 0.5× Opera®, showed a high level of disease control, especially at the 42 and 56 day time points. These results demonstrate that glyphosate treatment controls soybean rust disease in glyphosate tolerant soybean and the effect is synergistic when combined with a fungicide treatment.

Table 3. Greenhouse study of Glyphosate (glyp) and Opera® fungicide effects on the percent disease of Asian soybean rust on two treated Roundup Ready soybean cultivars.

TABLE 3

Greenhouse study of Glyphosate (glyp) and Opera fungicide effects on the percent disease of Asian soybean rust on two treated Roundup Ready soybean cultivars.

| RR cultivars | | 14 d-1 spray | 28 d-2 sprays | 42 d-3 sprays | 56 d-4 sprays |
|---|---|---|---|---|---|
| RR8000 | Trt 1 No spray | 40.0 | 56.7 | 71.7 | 81.7 |
| | Trt 2 glyp 1X | 23.3 | 41.7 | 48.3 | 88.3 |
| | Trt 3 glyp 2X | 10.0 | 10.0 | 10.0 | 30.0 |
| | Trt 4 Opera ® 1X | 3.3 | 3.3 | 6.7 | 13.3 |
| | Trt 5 Opera ® .5X | 10.0 | 10.0 | 23.3 | 30.0 |
| | Trt 6 glyp1X + Opera ® 0.5X | 10.0 | 10.0 | 10.0 | 13.3 |
| RR8045 | Trt 1 No spray | 56.7 | 71.7 | 81.7 | 93.3 |
| | Trt 2 glyp 1X | 50.0 | 56.7 | 71.7 | 86.7 |
| | Trt 3 glyp 2X | 3.3 | 10.0 | 13.3 | 73.3 |
| | Trt 4 Opera ® 1X | 6.7 | 10.0 | 16.7 | 16.7 |
| | Trt 5 Opera ® .5X | 10.0 | 13.3 | 26.7 | 33.3 |
| | Trt 6 glyp1X + Opera ® 0.5X | 3.3 | 10.0 | 13.3 | 13.3 |

A field study was conducted to further confirm the greenhouse study. The same cultivars were planted in three replicated plots and treatments as described in the greenhouse study. Table 4 shows the result of the field study demonstrating that glyphosate treatment substantially reduces the percent disease due to Asian soybean rust infection. Glyphosate+fungicide treatment of RR8000 showed a synergistic effect (13.3%) in reducing disease when compared to the glyphosate 1× rate (23.3%) and Opera® 0.5× (21.7%) rate treatments. All treatments were effective in preventing disease on RR8045 cultivar. These results provide further evidence that glyphosate is useful to control Asian soybean rust disease in glyphosate tolerant soybeans in a field environment and that an admixture of glyphosate and a fungicide is particularly effective.

Table 4 Field trial Glyphosate (glyp) and Opera® fungicide effects on the percent disease of Asian soybean rust on two treated Roundup Ready soybean cultivars.

TABLE 4

Field trial Glyphosate (glyp) and Opera fungicide effects on the percent disease of Asian soybean rust on two treated Roundup Ready soybean cultivars

| cultivar | treatment | %_disease |
|---|---|---|
| RR8000 | No spray | 50.0 |
| | glyp 1X | 23.3 |
| | glyp 2X | 10.0 |
| | Opera ® 1X | 6.7 |
| | Opera ® .5X | 21.7 |
| | glyp1x + Opera ® 0.5X | 13.3 |
| RR8045 | No spray | 60.0 |
| | glyp 1X | 0.0 |
| | glyp 2X | 1.7 |
| | Opera ® 1X | 0.0 |
| | Opera ® .5X | 0.0 |
| | glyp1x + Opera ® 0.5X | 3.3 |

Roundup WeatherMAX® (WMAX) tank mixes with fungicides, insecticides or both are tested for use in soybean.

Soybean rust is a significant problem disease in South America and serious concern in the U.S. Testing is conducted to develop a method for use of mixtures of the WMAX formulation of glyphosate and various commercially available fungicides for weed control and soy rust control as listed in Table 5. The fields are planted with Roundup Ready® soybeans after use of tillage or Roundup WMAX to reduce weeds. All plots receive a post plant application of Roundup WMAX about 3 weeks after planting. The mixtures of WMAX alone or WMAX+fungicide are used to treat the plots at the R1 stage of soybean development (first flowering) of treatment are listed in Table 5. Data is taken for percent weed control at 7 and 21 days after R1 treatment, soybean safety (% necrosis, chlorosis, growth rate): 5 days after treatment, disease rating, and soybean yield (bushels/Acre). These mixtures and treatments are designed to provide simultaneous weed and pest control of soybean, such as fungal pest control, for example, soybean rust disease; and insect pest control, for example, aphid control.

TABLE 5

Glyphosate plus pesticide mixtures (fungicides and an insecticide)

| mix | R1, flowering | 14 to 21 days after R1 |
|---|---|---|
| 1 | WMAX | |
| 2 | | WMAX |
| 3 | WMAX + Quadris ® | |
| 4 | WMAX + Bravo ® | |
| 5 | WMAX + Stratego ® | |
| 6 | WMAX + Tilt ® | |
| 7 | WMAX + Folicur ® | |
| 8 | WMAX + Headline ® | |
| 9 | | WMAX + Quadris ® |
| 10 | | WMAX + Bravo ® |
| 11 | | WMAX + Stratego ® |
| 12 | | WMAX + Tilt ® |
| 13 | | WMAX + Folicur ® |
| 14 | | WMAX + Headline ® |
| 15 | WMAX + Warrior ® + Quadris ® | |
| 16 | WMAX + Warrior ® | |

Agricultural chemicals are provided in containers suitable for safe storage, transportation and distribution, stability of the chemical compositions, mixing with solvents and instructions for use. The present invention provides for a container of a mixture of a glyphosate compound and a fungicide compound, or a mixture of a glyphosate compound and an insecticide compound, or a mixture of a glyphosate compound and a fungicide compound and an insecticide compound (Warrier®). The container may further provide instructions on the effective use of the mixture. Containers of the present invention can be of any material that is suitable for the storage of the chemical mixture. Containers of the present invention can be of any material that is suitable for the shipment of the chemical mixture. The material can be of cardboard, plastic, metal, or a composite of these materials. The container can have a volume of 0.5 liter, 1 liter, 2 liter, 3-5 liter, 5-10 liter, 10-20 liter, 20-50 liter or more depending upon the need. A tank mix of a glyphosate compound and a fungicide compound is provided, methods of application to the crop to achieve an effective dose of each compound are known to those skilled in the art and can be refined and further developed depending on the crop, weather conditions, and application equipment used.

Example 9: Glyphosate to Prevent or Control Rust of Corn

*Puccinia sorghi* is the fungus causing Common rust disease in corn and Southern rust disease is caused by the fungus *Puccinia polysora*. Field tests were conducted to determine if glyphosate treatment of Roundup Ready® corn nk603 hybrid and inbred lines could reduce the incidence of disease caused by rust diseases of corn. The glyphosate tolerant corn plants and non-tolerant control plants were inoculated with Common rust or Southern rust spores.

The glyphosate was applied as a formulation of Roundup® WeatherMAX® (4.5 lbs./Gal, 49% a.i.) from a CO2 backpack sprayer with a 2-nozzel boom (8002 nozzle) at 30 pounds per square inch. The treatment was pre-inoculation (treatment #1, approximately 5 hours before the inoculation of the rust spores), 14 days post inoculation (treatment #2), and 28 days post inoculation (treatment #3). Glyphosate was applied at a 2× rate (1.5 lb./A) and a 3× rate (2.25 lb./A) at each treatment time. Two hybrid corn lines (DKC53-33 and DKC60-09) and two inbred corn lines ((87DIA4NK603A and 90DJD28NK603A) were tested in the experimental plots. The plot size was 2 rows at 10 replications=20 rows per treatment at 2.5 ft/per row=50 ft. wide at 15 ft. length=750 sq. ft./43,560 sq. ft./Acre=0.0172 Acres/Treatment. Disease ratings were taken on a 1 to 9 scale where 1=resistant and 9=susceptible. The rating used in the analysis is the average of the last three rating dates (approximated 5 weeks post inoculation, 7 weeks post inoculation and 9 weeks post inoculation).

The results of the hybrid corn test showed the control plots with an average disease rating of 4.1 for each line and treatment #1 at the 2× rate with an average disease rating of 3.6 and a disease rating of 3.0 at the 3× rate. Treatment #2 and #3 had a disease rating of 4.1 and 3.9 respectively. The inbred corn test showed the control plots with an average disease rating of 5.0 and 4.9 for each line and treatment #1 with an average disease rating of 4.0 at the 2× rate and 3.2 for the 3× rate. The post inoculation treatments showed a disease rating of 4.4 and 4.9.

Natural Common rust infection occurred prior to the artificial inoculations in these tests, therefore the controls (uninoculated/unsprayed, and inoculated/unsprayed) showed about the same disease rating. These results demonstrated that glyphosate treatment reduces disease severity of corn rusts, especially when applied early in the infection process.

Example 10: *Verticillium* Wilt Control in Roundup Ready® Cotton

*Verticillium* wilt is a soil borne fungal vascular wilt pathogen that attacks over 300 woody and herbaceous host plants. Especially important are members of the Solanaceous plant family, for example, tomato, potato, and eggplant. Other crops of importance are alfalfa, sunflower, peanuts, and cotton. *Verticillium dahliae* is the causal organism for *Verticillium* wilt of cotton.

The ability of glyphosate to provide reduction in disease symptoms of *Verticillium* wilt of cotton was tested with Roundup Ready® cotton in three genetic backgrounds. The cotton seeds were planted and the emerged plants were sprayed with 22 ounces of WeatherMax Roundup® at the two and five true leaf stage. Plants were observed for wilt symptoms approximately three months and four months after planting. The glyphosate treated plants showed reduced symptoms and were more vigorous than the plants in the adjacent untreated plot. The treated plants continued to grow compared to the untreated plants that had shut down. The observation indicates that moderately *Verticillium* resistant and susceptible cotton lines with glyphosate tolerant genetic backgrounds with benefit from glyphosate treatment to reduce the severity of *Verticillium* wilt disease. Cotton plants suffering from other wilt diseases of cotton, especially *Fusarium* wilt disease, are expected to benefit from treatment with glyphosate.

Example 11

Plant 5-enolpyruvylshikimate-3-phosphate synthase (EPSPS) enzymes are very sensitive to glyphosate and kinetic studies have shown that corn EPSPS has a Ki for glyphosate of 0.5 μM, which is equivalent to approximately 0.15 ppm of glyphosate in plant tissues. Structural studies of EPSPS based on X-ray crystallography have identified key amino acids involved in catalysis. These amino acids are highly conserved across species and have been used to characterize the interactions between glyphosate and EPSPS. In fact, the presence of 4 unique amino acid motifs has been used to classify the EPSPS enzymes into glyphosate sensitive or resistant variants (U.S. Pat. No. 5,633,435). A search of public databases showed genomic sequences from twelve fungi shown in Table 6. We deduced and aligned the amino acid sequences of the fungal EPSPSs and conclude that all twelve are classified as glyphosate sensitive. The presence of a glyphosate-sensitive EPSPS is necessary for glyphosate to have activity against a fungal pest, although other processes present in the fungal pest cell could influence the level of effect that glyphosate would have, such as, the presence of a glyphosate metabolism process, or glyphosate transport, or sequestering process. The result of our analysis indicates that fungi are likely to posses a glyphosate-sensitive EPSPS, which would translate to inhibition or suppression of fungal cell growth and development when treated with a glyphosate composition.

TABLE 6

| EPSPS gene id | Fungus Genus species name |
|---|---|
| gi\|6320332 | *Saccharomyces cerevisiae* |
| gi\|45201161 | *Eremothecium gossypii* |
| gi\|46444923 | *Candida albicans* SC5314 |
| gi\|19115593 | *Schizosaccharomyces pombe* |
| gi\|6226554 | *Aspergillus nidulans* |
| gi\|44889967 | *Aspergillus fumigatus* |
| gi\|38102656 | *Magnaporthe grisea* 70-15 |
| gi\|32415183 | *Neurospora crassa* |
| gi\|46116890 | *Gibberella zeae* PH-1 |
| gi\|49074134 | *Ustilago maydis* 521 |
| gi\|25005077 | *Thanatephorus cucumeris* |
| gi\|2492977 | *Pneumocystis carinii* |
| gi\|31087950 | *Puccinia triticina* |

All publications, patents and patent applications are herein incorporated by reference to the same extent as if each individual publication or patent application was specifically and individually indicated to be incorporated by reference.

We claim:

1. A method for treating leaf rust disease in a soybean or corn plant or wilt disease in a cotton plant comprising, identifying a soybean or corn plant as being infected with a rust pathogen, or a cotton plant as being infected with a wilt pathogen; and applying a composition having glyphosate to said soybean, corn, or cotton plant or portion thereof, further wherein the composition comprises at least one fungicide selected from the group consisting of: a strobilurin and epoxiconazole;

whereby said composition results in said disease being controlled.

2. The method of claim 1, wherein the strobilurin is pyraclostrobin.

3. A method of controlling weeds and Soybean Rust disease in a field of glyphosate tolerant soybean plants, weeds and corn rust in a field of glyphosate tolerant corn plants, or weeds and cotton wilt disease in a field of glyphosate tolerant cotton plants, said method comprising, identifying a soybean or corn plant as being infected with a rust pathogen, or a cotton plant as being infected with a wilt pathogen applying a first composition to the field, comprising a first glyphosate composition comprising an effective amount to control said weeds; and applying a second composition to the field, comprising an effective amount of a second glyphosate composition, whereby said second composition comprises a fungicide containing pyraclostrobin and epoxiconazole and controls said disease of said plants.

4. A method of controlling weeds and Soybean Rust disease in a field of glyphosate tolerant soybean plants, said method comprising, identifying a soybean plant as being infected with Soybean Rust;

applying a first composition to the field, comprising a first glyphosate composition comprising an effective amount to control said weeds; and applying a second composition to the field, comprising an effective amount of a second glyphosate composition, wherein said second composition also comprises at least one fungicide selected from the group consisting of: a strobilurin and epoxiconazole; and controls said disease of said plants.

5. The method of claim 4, wherein the strobilurin is pyraclostrobin.

* * * * *